United States Patent
Ackerman et al.

(10) Patent No.: US 12,378,305 B2
(45) Date of Patent: Aug. 5, 2025

(54) COMPOSITIONS AND METHODS FOR PREVENTING OR AMELIORATING NEONATAL HSV INFECTION

(71) Applicants: Trustees of Dartmouth College, Hanover, NH (US); Duke University, Durham, NC (US)

(72) Inventors: Margaret E. Ackerman, Hanover, NH (US); Iara M. Backes, Hanover, NH (US); David A. Leib, Hanover, NH (US); Chaya D. Patel, Hanover, NH (US); Michael Anthony Moody, Durham, NC (US)

(73) Assignees: Trustees of Dartmouth College, Hanover, NH (US); Duke University, Durham, NC (US)

( * ) Notice: Subject to any disclaimer, the term of this patent is extended or adjusted under 35 U.S.C. 154(b) by 1091 days.

(21) Appl. No.: 17/284,427

(22) PCT Filed: Oct. 10, 2019

(86) PCT No.: PCT/US2019/055685
§ 371 (c)(1),
(2) Date: Apr. 9, 2021

(87) PCT Pub. No.: WO2020/077119
PCT Pub. Date: Apr. 16, 2020

(65) Prior Publication Data
US 2021/0340223 A1    Nov. 4, 2021

Related U.S. Application Data

(60) Provisional application No. 62/744,325, filed on Oct. 11, 2018.

(51) Int. Cl.
| | | |
|---|---|---|
| *C07K 16/00* | (2006.01) | |
| *A61K 39/245* | (2006.01) | |
| *A61P 25/22* | (2006.01) | |
| *A61P 31/22* | (2006.01) | |
| *C07K 16/08* | (2006.01) | |
| *A61K 39/00* | (2006.01) | |
| *A61K 48/00* | (2006.01) | |

(52) U.S. Cl.
CPC .......... *C07K 16/087* (2013.01); *A61K 39/245* (2013.01); *A61P 25/22* (2018.01); *A61P 31/22* (2018.01); *A61K 2039/5254* (2013.01); *A61K 2039/55* (2013.01); *A61K 48/00* (2013.01); *C07K 2317/56* (2013.01); *C07K 2317/565* (2013.01)

(58) Field of Classification Search
CPC .............. C07K 16/087; C07K 2317/56; C07K 2317/565; C07K 2317/76; A61K 39/245; A61K 48/00; A61K 2039/5254; A61K 2039/55; A61K 39/12; A61K 2039/505; A61P 25/22; A61P 31/22; C12N 2710/16634
See application file for complete search history.

(56) References Cited

U.S. PATENT DOCUMENTS

| | | | |
|---|---|---|---|
| 2003/0165819 A1* | 9/2003 | McGowan | C07K 14/005 435/69.3 |
| 2010/0172906 A1* | 7/2010 | Lai | A61P 31/22 435/254.2 |
| 2012/0282260 A1 | 11/2012 | Lai et al. | |
| 2014/0302062 A1* | 10/2014 | Haynes | C07K 16/087 536/23.53 |
| 2016/0000797 A1* | 1/2016 | Checcone | A61K 31/565 424/432 |

FOREIGN PATENT DOCUMENTS

| | | |
|---|---|---|
| EP | 2526966 B1 | 3/2016 |
| WO | WO 2017/189964 A2 | 11/2017 |
| WO | WO 2020/077119 A1 | 4/2020 |

OTHER PUBLICATIONS

Fuchs et al. (Methods and Clinical Development, 3: 1-18, 2016).*
Da Costa et al. (Journal of Virology, 74(17): 7963-7971, 2000).*
Agvil et al. (Reproductive Toxicology, 21: 436-445, 2006).*
Coughlin, *Public Health Reviews*, 34(2): 1-17 (2012).
Da Costa, *Journal of Virology*, 74(17): 7963-7971 (2000).
Evans, *The Journal of Infectious Diseases*, 185: 1550-1560 (2002).
Jiang et al., *Future Virology*, 12(12): 709-711 (2017).
Jiang et al., *mBio*, 8(4):e00678-17 (Jul./Aug. 2017).
Patel et al., *Sci. Transl. Med.*, 11(487): 1-22 (2019).
Wang et al., *Journal of Virology*, 91(19): 1-14 (2017).
The United States Patent and Trademark Office, International Search Report for International Application No. PCT/US2019/055685 (Jan. 7, 2020).
The United States Patent and Trademark Office, Written Opinion of The International Searching Authority for International Application No. PCT/US2019/055685 (Jan. 7, 2020).

* cited by examiner

*Primary Examiner* — Nelson B Moseley, II
(74) *Attorney, Agent, or Firm* — Neal, Gerber & Eisenberg LLP

(57) ABSTRACT

The present disclosure relates to compositions and methods for treating or preventing neonatal herpes simplex virus (HSV) infection and/or the neurological and/or non-neurological sequelae thereof.

23 Claims, 11 Drawing Sheets
Specification includes a Sequence Listing.

COMPOSITIONS AND METHODS FOR PREVENTING OR AMELIORATING NEONATAL HSV INFECTION

CROSS REFERENCE TO RELATED APPLICATIONS

This patent application is a National Stage Entry of International Application No. PCT/US2019/055685, filed on Oct. 10, 2019, which claims priority to U.S. Provisional Patent Application No. 62/744,325, filed on Oct. 11, 2018, the entire contents of which are fully incorporated herein by reference.

FEDERALLY SPONSORED RESEARCH OR DEVELOPMENT

Not applicable.

TECHNICAL FIELD

The present invention relates to compositions and methods for preventing, or ameliorating the neurological and/or non-neurological sequelae of, neonatal herpes simplex virus (HSV) infection.

BACKGROUND

Herpes simplex virus 1 and 2 (collectively, "HSV") are species in the herpesvirus family, Herpesviridae. Herpesviruses are enveloped double-stranded DNA viruses. The envelope is studded with glycoproteins, which can serve as targets for antibodies.

About ⅔ of the population in the United States is seropositive for HSV-1, and HSV infection is life-long. One of the hallmarks of HSV infection is the ability of the virus to enter a state of latency, which may be followed by a state of reactivation.

Primary HSV infection is typically established in epithelial cells, which are the site of acute viral replication. Upon subsequent infection of innervating sensory neurons, the virus travels, via retrograde axonal transport, to the soma of neurons where it can establish latent infection. Reactivation, and resumption of lytic replication, involves anterograde transport of the virus toward peripheral epithelial cells resulting in recurrent symptoms and/or asymptomatic viral shedding.

Clinically evident HSV infection can present itself as a common cold sore. Most HSV infections in immunocompetent adults are not life threatening. However, the disease can have a deadly manifestation in immunocompromised individuals and neonates.

Neonatal HSV infection is one of the most feared pediatric infections. It occurs in approximately 1:3200 live births in the US. The current standard of care is acyclovir (ACV) treatment but requires a high degree of clinical suspicion, and symptoms are often non-specific. Even with aggressive ACV treatment more than 50% of infected babies go on to develop disseminated infection and encephalitis. Mortality is high and surviving infants with central nervous system (CNS) involvement suffer long-term neurodevelopmental disabilities, incurring significant economic burden.

Therefore, there is a need for new compositions and methods for preventing, or ameliorating the effect, particularly the neurological sequelae of, neonatal HSV infection.

SUMMARY OF THE INVENTION

In one aspect, this disclosure provides a method for preventing, or ameliorating the effects of, a neonatal viral infection, particularly infection by a vertically transmitted pathogen such as herpesvirus, and more particularly a HSV infection, such as an HSV-1 or HSV-2 infection. In certain embodiments, the method comprises immunizing a maternal subject with an anti-herpesvirus antibody, wherein the maternal subject is pregnant or likely to become pregnant. In some such embodiments, the immunization is active immunization (e.g., administration of a herpesvirus antigen or a replication-impaired herpesvirus to the maternal subject, preferably in combination with an adjuvant). Thus, the method may comprise administering an HSV antigen or a replication-impaired HSV to the maternal subject. In other such embodiments, the immunization is passive immunization (e.g., administration of an anti-herpesvirus antibody to the maternal subject). Thus, the method may comprise administering an anti-HSV antibody to the maternal subject. In certain embodiments, the maternal subject is HSV seronegative. In certain other embodiments, the maternal subject is suspected of having a primary HSV infection.

In certain embodiments, the method comprises administering to a maternal subject (1) an immunogenic product having one or more HSV antigens and/or (2) an anti-HSV antibody. In some such embodiments, the immunogenic product is an HSV protein, such as glycoprotein D (gD), or an antigenic fragment thereof. In some such embodiments, the immunogenic product is a live-attenuated or replication-impaired HSV, such as dl5-29. In some such embodiments, the anti-HSV antibody is a neutralizing antibody. In some such embodiments, the anti-HSV antibody blocks the interaction between gD and herpesvirus entry mediator (HVEM). In some such embodiments, the anti-HSV antibody is a monoclonal antibody (mAb). For example, the anti-HSV antibody may be mAb 5188 (also known as CH42), which binds gD residues that interface with the herpes virus entry mediator (HVEM) receptor (Wang et al. JVi, 2017). Alternatively, the anti-HSV antibody may be mAb E317. In certain embodiments, the HSV antigen and/or the anti-HSV antibody are administered to the maternal subject prior to parturition.

In one aspect, this disclosure provides a method for preventing, or ameliorating the effects of, a neonatal HSV infection by administering an anti-HSV antibody to a maternal subject, wherein the maternal subject is pregnant or likely to become pregnant. In certain embodiments, the maternal subject is pregnant. In certain embodiments, the anti-HSV antibody is specific for glycoprotein D (gD) of HSV. In certain embodiments, the anti-HSV antibody is a monoclonal antibody that is specific for gD of HSV. In certain embodiments, the anti-HSV antibody is a monoclonal antibody that is specific for gD of HSV and blocks the interaction between gD and HVEM. Without wishing to be bound by theory, administration of the anti-HSV antibody may prevent mortality and/or the neurological/behavioral pathology resulting from neonatal herpes simplex infection by maternal transfer of the antibody.

In one aspect, this disclosure provides a method for preventing, or ameliorating the effects of, a neonatal HSV infection by administering an anti-HSV antibody to the neonate. In certain embodiments, the anti-HSV antibody is specific for glycoprotein D (gD) of HSV. In certain embodiments, the anti-HSV antibody is a monoclonal antibody that is specific for gD of HSV. In certain embodiments, the anti-HSV antibody is a monoclonal antibody that is specific for gD of HSV and blocks the interaction between gD and HVEM. In certain embodiments, the neonate is infected with HSV. In certain embodiments, the neonate is suspected to be infected with HSV. In certain embodiments, the neonate is septic. In certain embodiments, acyclovir is also administered to the neonate.

In one aspect, this disclosure provides a method for preventing, or ameliorating the effects of, a neonatal HSV infection by administering an HSV vaccine to a maternal subject, wherein the maternal subject is pregnant or likely to become pregnant. In certain embodiments, the maternal subject is pregnant. In certain embodiments, the HSV vaccine is a replication-impaired HSV. Without wishing to be bound by theory, administration of the HSV vaccine may prevent mortality and/or the neurological/behavioral pathology resulting from neonatal herpes simplex infection by eliciting maternal anti-HSV antibodies and subsequent maternal transfer of the antibody to the neonate.

In one aspect, this disclosure provides an immunogenic product comprising one or more herpesvirus antigens or an anti-herpesvirus antibody for use in a method for preventing, or ameliorating the effects of, a neonatal HSV infection. In certain embodiments, the immunogenic product is an HSV protein, such as glycoprotein D (gD), or an antigenic fragment thereof. In certain embodiments, the immunogenic product is a live-attenuated or replication-impaired HSV, such as dl5-29. In certain embodiments, the anti-HSV antibody is a neutralizing antibody. In certain embodiments, the anti-HSV antibody blocks the interaction between gD and herpesvirus entry mediator (HVEM). In certain embodiments, the anti-HSV antibody is a monoclonal antibody (mAb). For example, the anti-HSV antibody may be mAb 5188 (also known as CH42), which binds gD residues that interface with HVEM. Alternatively, the anti-HSV antibody may be mAb E317, which binds gD.

The antibodies and vaccines, pharmaceutical compositions comprising the antibodies and/or vaccines, and methods for preventing, or ameliorating the effects of, a neonatal HSV infection by administering the antibodies and/or vaccines are further described herein.

These and other objects of the invention are described in the following paragraphs. These objects should not be deemed to narrow the scope of the invention.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art.

DETAILED DESCRIPTION

Figure 1A:
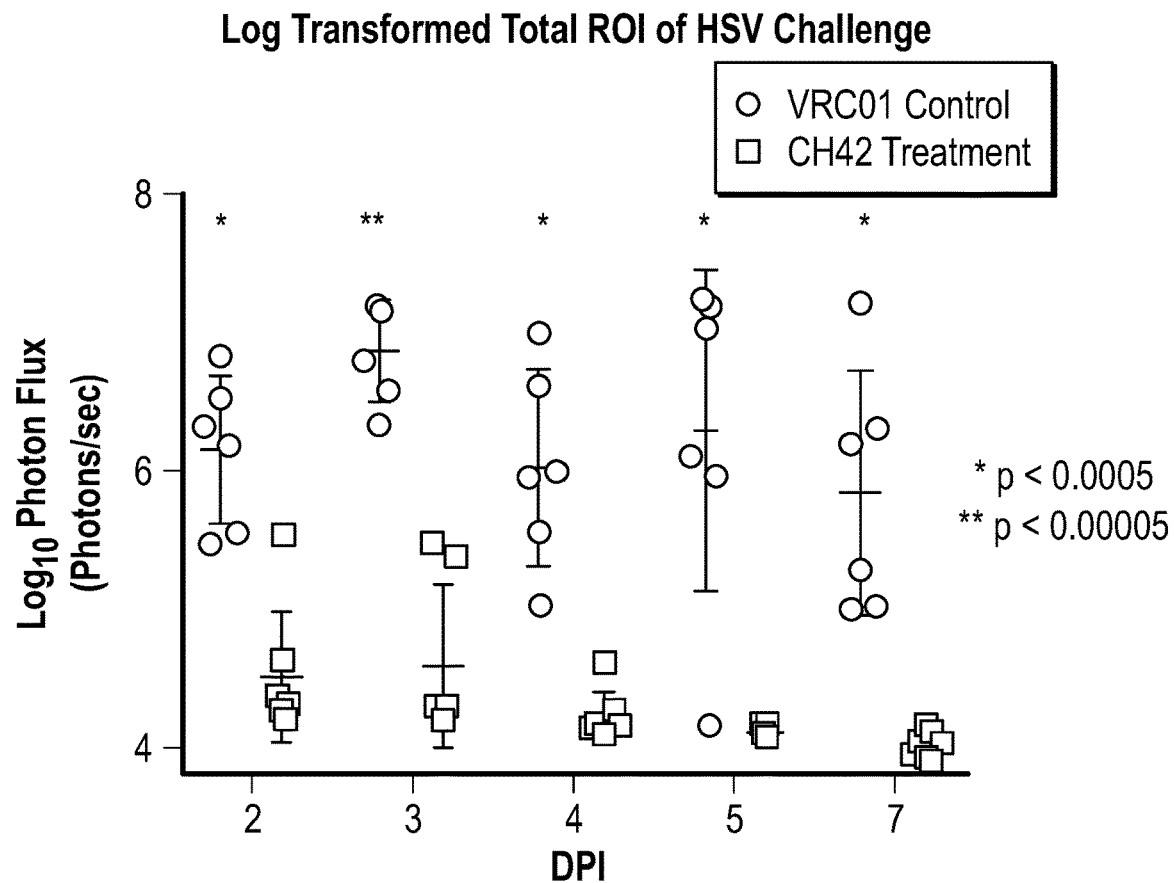
FIG. 1A is a plot showing quantification of total luminescence on pups challenged with HSV-1 st 17 expressing luciferase (st17dlux). Dams were administered an anti-HSV antibody (CH42) or a control antibody (VRC01).

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "adjuvant" refers to agents or compounds that prolong, enhance, and/or accelerate an immune response.

The term "antibody" includes a glycoprotein comprising at least two heavy (H) chains and two light (L) chains inter-connected by disulfide bonds, or an immunologically effective fragment thereof. The term "immunologically effective (antibody) fragment" as used herein refers to a portion of an intact antibody comprising the antigen-binding site or variable region. The portion does not necessarily include the constant heavy chain domains (i.e., CH2, CH3 or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The term "CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non-human source. However the definition is not limited to this particular example.

The term "gD" refers to HSV envelope glycoprotein encoded by US6 gene. The HSV gD glycoprotein is a multifunction protein with that helps to define viral host tropism. As used herein, the term "gD" includes isolated mature glycoprotein, peptide fragments thereof (e.g., truncated forms), and fusion protein formed with gD or a fragment thereof and another peptide. An exemplary gD protein is the HSV-1 gD protein, referred to herein as "gD1." Another exemplary gD protein is the HSV-2 gD protein, referred to as "gD2." As an example, a gD protein may have at least 90%, at least 95%, or at least 97%, or at least 98%, or at least 99%, or 100% identity with the sequence of SEQ ID NO: 18 and/or SEQ ID NO: 19.

The term "herpesvirus" refers to a group of viruses belonging to the family Herpesviridae and, in particular, those viruses in which humans are the primary host. Humans are the primary host for several herpesviruses, including herpes simplex virus 1 (HSV-1), herpes simplex virus 2 (HSV-2), varicella-zoster virus (VZV), Epstein-Barr virus (EBV), human cytomegalovirus (HCMV), human herpesvirus 6A and 6B (HHV-6A and HHV-6B), human herpesvirus-7 (HHV-7), and Kaposi's sarcoma herpes virus (KSHV). Throughout the application, "HSV" is used to collectively refer to HSV-1 and HSV-2.

The term "human antibody" includes antibodies having variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions (e.g., modified to resemble human immunoglobulins more closely). Some forms of humanized antibodies preserve all CDR sequences (for example a humanized mouse antibody which contains all six CDRs from the mouse antibody). Other forms have one or more CDRs which are altered with respect to the original antibody.

The terms "immunization" or "vaccination" describe the process of administering one or more antigens to an individual with the purpose of inducing an immune response, for example, for therapeutic or prophylactic reasons.

The term "maternal subject" includes humans and other primates as well as other mammals. The term maternal subject includes, for example, a premenopausal female. In certain embodiments, the maternal subject is a human. In certain embodiments, the maternal subject is a human female of reproductive age. In some such embodiments, the maternal subject is HSV seronegative. In some such embodiments, the maternal subject is suspected of having a primary HSV infection.

The terms "treat", "treating" and "treatment" refer to both therapeutic and preventative or prophylactic measures to alleviate or abrogate a condition, disorder, or disease and/or the attendant symptoms thereof.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

B. ANTI-HERPESVIRUS ANTIBODIES

In one aspect, the present disclosure provides methods and compositions for passive immunization. In this aspect, the methods and compositions described herein utilize or comprise an anti-herpesvirus antibody, such as an anti-HSV antibody.

In certain embodiments, anti-herpesvirus antibodies useful herein include those antibodies which have been isolated, characterized, purified, are functional and have been recovered (obtained) for use in a functional therapeutic composition which is administered to a living subject.

In certain embodiments for any of the aspects described herein, the anti-herpesvirus antibody is an anti-HSV antibody. In some such embodiments, the anti-HSV antibody specifically binds to an HSV protein or a fragment thereof. In some such embodiments, the anti-HSV antibody specifically binds to HSV gD or a fragment thereof. The anti-gD antibody may be a neutralizing antibody that, for example, blocks HSV binding to HVEM. Exemplary anti-gD antibodies include DL11, 1D3, 5157, 5158, 5159, 5160, 5188, 5190, 5192, E317, E425 and Y571, which are identified in, for example, Nicola, et al., J Virol, 72(5):3595-3601 (1998), US 2014/0302062 (Haynes), and U.S. Pat. No. 8,252,906 (Lai) each of which is herein incorporated by reference in its entirety.

For example, in some such embodiments, the anti-HSV antibody binds to an epitope located at the N terminus of HSV-1 gD. In a particular embodiment, the anti-HSV antibody binds to an epitope located within amino acids 12 to 16 (ADPNR; SEQ ID NO: 9) of HSV-1 gD.

For example, according to US 2014/0302062 (Haynes), which is herein incorporated by reference in its entirety, mAb 5188 (CH42) comprises a heavy chain variable region having an amino acid sequence corresponding to H005188 (SEQ ID NO: 7) and a light chain variable region having an amino acid sequence corresponding to K003946 (SEQ ID NO: 8).

Thus, in certain embodiments, the methods and compositions described herein utilize or comprise (i) mAb 5188, (ii) an antibody having the heavy chain variable region and light chain variable region of mAb 5188, (iii) an antibody having the heavy chain CDRs (i.e., SEQ ID NOs: 1-3) and the light chain CDRs (i.e., SEQ ID NOs: 4-6) of mAb 5188, and/or (iv) an antibody having the binding specificity of mAb 5188.

The anti-HSV antibody may specifically bind to an HSV protein, such as gD, a fragment thereof, or a variant thereof and comprise a variable heavy chain and/or variable light chain shown in Table 1. The anti-HSV antibody may specifically bind to an HSV protein, such as gD, a fragment thereof, or a variant thereof and comprise the heavy chain CDRs and/or light chain CDRs shown in Table 1.

TABLE 1

List of Amino Acid Sequences of VH and VL Regions of Anti-gD Monoclonal Antibody (mAb) 5188 (CH42).

| PROTEIN REGION | SEQ ID NO. | SEQUENCE |
| --- | --- | --- |
| H005188 (VH)-CDR1 | 1 | SDYWMS |
| H005188 (VH)-CDR2 | 2 | NIKYDGSEKYYVDSVK |
| H005188 (VH)-CDR3 | 3 | AGLLWFGEKAFDI |
| K003946 (VL)-CDR1 | 4 | SRYLA |
| K003946 (VL)-CDR2 | 5 | YDASNRATGIP |
| K003946 (VL)-CDR3 | 6 | QQRRSWPPT |
| H005188 (VH) | 7 | EVQLVESGGG LVQPGGSLRL SCAASGFTFS DYWMSWVRQA PGKGLEWVAN IKYDGSEKYY VDSVKGRFTT SRDNAKNSLY LQMNSLRAED TAVYYCAGLL WFGEKAFDIW GQGTMVTVSS |
| K003946 (VL) | 8 | EIVLTQSPAT LSLSPGERAT LSCRASQNVS RYLAWYQQKP GQAPRLLIYD ASNRATGIPA RFSGSGSGTD FTLTISSLEP EDFAVYYCQQ RRSWPPTFGG GTKVEIK |

As another example, in some such embodiments, the anti-HSV antibody binds to a conformational epitope located on the α3-helix external surface of gD. In a particular embodiment, the anti-HSV antibody binds to an epitope comprising a continuous linear peptide from residues 221 to 224 (PRFI), residues Asn227, Val231 and Ser235 on helix α3, and/or residues Gln27, Tyr38, Asp139, Ser140, Asp215 and Ile238 of HSV-2 gD.

For example, according to U.S. Pat. No. 8,252,906 (Lai) and Lee, et al., Acta Crystallogr D Biol Crystallogr. 69(10): 1935-1945 (2013), each of which is herein incorporated by reference in its entirety, mAb E317 comprises a heavy chain variable region having an amino acid sequence corresponding to SEQ ID NO: 16 and a light chain variable region having an amino acid sequence corresponding to SEQ ID NO: 17.

Thus, in certain embodiments, the methods and compositions described herein utilize or comprise (i) mAb E317, (ii) an antibody having the heavy chain variable region and light chain variable region of mAb E317, (iii) an antibody having the heavy chain CDRs (i.e., SEQ ID NOs: 10-12) and the light chain CDRs (i.e., SEQ ID NOs: 13-15) of mAb E317 (according to the IMGT nomenclature), and/or (iv) an antibody having the binding specificity of mAb E317.

The anti-HSV antibody may specifically bind to an HSV protein, such as gD, a fragment thereof, or a variant thereof and comprise a variable heavy chain and/or variable light chain shown in Table 2. The anti-HSV antibody may specifically bind to an HSV protein, such as gD, a fragment thereof, or a variant thereof and comprise the heavy chain CDRs and/or light chain CDRs shown in Table 2.

TABLE 2

List of Amino Acid Sequences of VH and VL Regions of Anti-gD Monoclonal Antibody (mAb) E317.

| PROTEIN REGION | SEQ ID NO. | SEQUENCE |
|---|---|---|
| E317 (VH)-CDR1 | 10 | GGTLRTYG |
| E317 (VH)-CDR2 | 11 | TIPLFGKT |
| E317 (VH)-CDR3 | 12 | ARDLTTLTSYNWWDL |
| E317 (VL)-CDR1 | 13 | QSVTSSQ |
| E317 (VL)-CDR2 | 14 | GAS |
| E317 (VL)-CDR3 | 15 | QQYGSSPT |
| E317 (VH) | 16 | QVTLKQSGAE VKKPGSSVKV SCTASGGTLR TYGVSWVRQA PGQGLEWLGR TIPLFGKTDY AQKFQGRVTI TADKSMDTSF MELTSLTSED TAVYYCARDL TTLTSYNWWD LWGQGTLVTV S |
| E317 (VL) | 17 | EIVLTQSPGT LSLSPGERAT LSCRASQSVT SSQLAWYQQK PGQAPRLLIS GASNRATGIP DRFSGSGSGT DFTLTISRLE PEDFAVYYCQ QYGSSPTFGG GTKVEIKR |

In certain embodiments for any of the aspects described herein, the anti-HSV antibody is a monoclonal antibody. In certain embodiments for any of the aspects described herein, the anti-HSV antibody is a chimeric antibody, a single chain antibody, an affinity matured antibody, an Fc-modified antibody, an engineered antibody, a human antibody, a humanized antibody, or a fully human antibody. In certain embodiments for any of the aspects described herein, the anti-HSV antibody is an antibody fragment, such as a Fab, F(ab')$_2$, Fv or scFv fragment, or a mixture thereof.

An exemplary antibody useful herein comprises a tetramer. Each tetramer is composed of two pairs of polypeptide chains, each pair having one "light" (about 25 kDa) and one "heavy" chain (about 50-70 kDa). Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

In certain embodiments for any of the aspects described herein, the anti-HSV antibody comprises a set of six complementarity-determining regions, wherein (VH)-CDR1 has the amino acid sequence of SEQ ID NO: 1, (VH)-CDR2 has the amino acid sequence of SEQ ID NO: 2, (VH)-CDR3 has the amino acid sequence of SEQ ID NO: 3, (VL)-CDR1 has the amino acid sequence of SEQ ID NO: 4, (VL)-CDR2 has the amino acid sequence of SEQ ID NO: 5, and (VL)-CDR3 has the amino acid sequence of SEQ ID NO: 6.

In certain embodiments for any of the aspects described herein, the anti-HSV antibody comprises a heavy chain variable region (VH) having an amino acid sequence of SEQ ID NO: 7 or a fragment thereof.

In certain embodiments for any of the aspects described herein, the anti-HSV antibody comprises a light chain variable region (VL) having an amino acid sequence of SEQ ID NO: 8 or a fragment thereof.

In certain embodiments for any of the aspects described herein, the anti-HSV antibody comprises a heavy chain variable region (VH) having at least 70%, or at least 80%, or at least 85%, or at least 90%, or at least 95%, or at least 97%, or at least 98%, or at least 99% identity with the sequence of SEQ ID NO: 7.

In certain embodiments for any of the aspects described herein, the anti-HSV antibody comprises a light chain variable region (VL) having at least 70%, or at least 80%, or at least 85%, or at least 90%, or at least 95%, or at least 97%, or at least 98%, or at least 99% identity with the sequence of SEQ ID NO: 8.

In certain embodiments for any of the aspects described herein, the anti-HSV antibody is a chimeric antibody; for example, a chimeric form of CH42 comprising (i) a heavy chain having (a) a heavy chain variable region (VH) comprising SEQ ID NO: 7 and (b) a heavy chain constant region (CH) comprising an amino acid sequence derived from a human heavy chain constant region and (ii) a light chain having (c) a light chain variable region (VL) comprising SEQ ID NO: 8 and (d) a light chain constant region (CL) comprising an amino acid sequence derived from a human light chain constant region.

In certain embodiments for any of the aspects described herein, the anti-HSV antibody is a humanized antibody; for example, a humanized form of CH42 comprising (i) a heavy chain having (a) the heavy chain CDRs of CH42, (b) four FRs comprising an amino acid sequence derived from a human heavy chain FR, and (c) a heavy chain constant region (CH) comprising an amino acid sequence derived from a human heavy chain constant region and (ii) a light chain having (d) the light chain CDRs of CH42, (e) four FRs comprising an amino acid sequence derived from a human light chain FR, and (f) a light chain constant region (CL) comprising an amino acid sequence derived from a human light chain constant region.

In certain embodiments for any of the aspects described herein, the anti-HSV antibody comprises a set of six complementarity-determining regions, wherein (VH)-CDR1 has the amino acid sequence of SEQ ID NO: 10, (VH)-CDR2 has the amino acid sequence of SEQ ID NO: 11, (VH)-CDR3 has the amino acid sequence of SEQ ID NO: 12, (VL)-CDR1 has the amino acid sequence of SEQ ID NO: 13, (VL)-CDR2 has the amino acid sequence of SEQ ID NO: 14, and (VL)-CDR3 has the amino acid sequence of SEQ ID NO: 15.

In certain embodiments for any of the aspects described herein, the anti-HSV antibody comprises a heavy chain variable region (VH) having an amino acid sequence of SEQ ID NO: 16 or a fragment thereof.

In certain embodiments for any of the aspects described herein, the anti-HSV antibody comprises a light chain variable region (VL) having an amino acid sequence of SEQ ID NO: 17 or a fragment thereof.

In certain embodiments for any of the aspects described herein, the anti-HSV antibody comprises a heavy chain variable region (VH) having at least 70%, or at least 80%, or at least 85%, or at least 90%, or at least 95%, or at least 97%, or at least 98%, or at least 99% identity with the sequence of SEQ ID NO: 16.

In certain embodiments for any of the aspects described herein, the anti-HSV antibody comprises a light chain variable region (VL) having at least 70%, or at least 80%, or at least 85%, or at least 90%, or at least 95%, or at least 97%, or at least 98%, or at least 99% identity with the sequence of SEQ ID NO: 17.

In certain embodiments for any of the aspects described herein, the anti-HSV antibody is a chimeric antibody; for example, a chimeric form of E317 comprising (i) a heavy chain having (a) a heavy chain variable region (VH) comprising SEQ ID NO: 16 and (b) a heavy chain constant region (CH) comprising an amino acid sequence derived from a human heavy chain constant region and (ii) a light chain having (c) a light chain variable region (VL) comprising SEQ ID NO: 17 and (d) a light chain constant region (CL) comprising an amino acid sequence derived from a human light chain constant region.

In certain embodiments for any of the aspects described herein, the anti-HSV antibody is a humanized antibody; for example, a humanized form of E317 comprising (i) a heavy chain having (a) the heavy chain CDRs of E317, (b) four FRs comprising an amino acid sequence derived from a human heavy chain FR, and (c) a heavy chain constant region (CH) comprising an amino acid sequence derived from a human heavy chain constant region and (ii) a light chain having (d) the light chain CDRs of E317, (e) four FRs comprising an amino acid sequence derived from a human light chain FR, and (f) a light chain constant region (CL) comprising an amino acid sequence derived from a human light chain constant region.

Generally, a humanized antibody is produced from a monoclonal antibody raised initially in a non-human animal. As used herein humanized forms of non-human (e.g., murine) antibodies are chimeric antibodies that contain a minimal sequence derived from a non-human immunoglobulin. In one embodiment, a humanized antibody is a human immunoglobulin (recipient or acceptor antibody) in which residues from a CDR of the recipient antibody are replaced by residues from a CDR of a non-human species (donor antibody) such as mouse, rat, rabbit, or nonhuman primate having the desired specificity, affinity, and/or capacity.

Generally humanization of an antibody comprises an analysis of the sequence homology and canonical structures of both the donor and recipient antibodies. In selected embodiments, the recipient antibody may comprise consensus sequences. To create consensus human frameworks, frameworks from several human heavy chain or light chain amino acid sequences may be aligned to identify a consensus amino acid sequence. Moreover, in many instances, one or more framework residues in the variable domain of the human immunoglobulin are replaced by corresponding non-human residues from the donor antibody. These framework substitutions are identified by methods well known in the art, e.g., by modeling of the interactions of the CDR and framework residues to identify framework residues important for antigen binding and sequence comparison to identify unusual framework residues at particular positions. Such substitutions help maintain the appropriate three-dimensional configuration of the grafted CDR(s) and often improve infinity over similar constructs with no framework substitutions. Furthermore, humanized antibodies may comprise residues that are not found in the recipient antibody or in the donor antibody. These modifications may be made to further refine antibody performance using well-known techniques.

Human germline sequences, for example, are disclosed in Tomlinson, I. A. et al. (1992) J. Mol. Biol. 227:776-798; Cook, G. P. et al. (1995) Immunol. Today 16: 237-242; Chothia, D. et al. (1992). T. Mol. Bio. 227:799-817; and Tomlinson et al. (1995) EMBO. T 14:4628-4638. The V BASE directory provides a comprehensive directory of human immunoglobulin variable region sequences and includes a catalogue of all mapped V gene segments and alleles (see Retter et al., (2005) Nuc Acid Res 33: 671-674). These sequences can be used as a source of a human sequence (e.g., a human framework region sequence).

Antibodies described herein include polyclonal and monoclonal antibodies and include IgA such as IgA1 or IgA2, IgG1, IgG2, IgG3, IgG4, IgE, IgM, and IgD antibodies. In various embodiments, the antibody is an IgG1 antibody, more particularly an IgG1, kappa (i.e., IgG1κ) or IgG1, lambda isotype (i.e., IgG1λ), an IgG2a antibody, an IgG2b antibody, an IgG3 antibody, or an IgG4 antibody.

In one aspect, this disclosure provides a nucleic acid molecule encoding an antibody, preferably a monoclonal antibody or a fragment thereof, described herein.

In certain embodiments, the nucleic acid molecule comprises a nucleotide sequence encoding an anti-HSV antibody that comprises (i) a VH chain comprising three CDRs and (ii) a VL chain comprising three CDRs, wherein (VH)-CDR1 has the amino acid sequence of SEQ ID NO: 1, (VH)-CDR2 has the amino acid sequence of SEQ ID NO: 2, (VH)-CDR3 has the amino acid sequence of SEQ ID NO: 3, (VL)-CDR1 has the amino acid sequence of SEQ ID NO: 4, (VL)-CDR2 has the amino acid sequence of SEQ ID NO: 5, (VL)-CDR3 has the amino acid sequence of SEQ ID NO: 6. In certain embodiments, the nucleic acid molecule is contained in a vector.

In certain embodiments, the nucleic acid molecule comprises a nucleotide sequence encoding an anti-HSV antibody that comprises (i) a VH chain comprising three CDRs and (ii) a VL chain comprising three CDRs, wherein (VH)-CDR1 has the amino acid sequence of SEQ ID NO: 10, (VH)-CDR2 has the amino acid sequence of SEQ ID NO: 11, (VH)-CDR3 has the amino acid sequence of SEQ ID NO: 12, (VL)-CDR1 has the amino acid sequence of SEQ ID NO: 13, (VL)-CDR2 has the amino acid sequence of SEQ ID NO: 14, (VL)-CDR3 has the amino acid sequence of SEQ ID NO: 15. In certain embodiments, the nucleic acid molecule is contained in a vector.

Cloning techniques by Balazs et. al (Nature, 2012), which is herein incorporated by reference in its entirety, can be used to provide an in vivo monoclonal antibody expression system, which allows for long lasting antibody expression. This system has been successfully used to generate protective human immunodeficiency virus specific mAbs in the mouse and non-human primate model in preclinical trials, and has an ongoing clinical trial.

C. HERPESVIRUS VACCINES

In one aspect, the present disclosure provides methods and compositions for active immunization. In this aspect, the methods and compositions described herein utilize or comprise an immunogenic product, which, when administered to a subject, elicits an immune response, particularly a humoral immune response, against a herpesvirus, such as HSV-1 and/or HSV-2.

In certain embodiments, the immunogenic product comprises one or more herpesvirus peptides or proteins (e.g., a gD polypeptide or an antigenic portion thereof); an inactivated viral preparation; a live-attenuated herpesvirus; a replication-impaired herpesvirus; or a combination thereof.

In some such embodiments, the immunogenic product includes a herpesvirus protein or an antigenic portion thereof. For example, the immunogenic product may include herpesvirus protein subunits (e.g., HSV glycoproteins gB, gC, gD, and/or gE) or portions thereof.

In an exemplary embodiment, the immunogenic product includes antigenic epitopes of a herpesvirus protein, such as HSV gD. For example, the immunogenic product may include gD truncated at, for example amino acid 234 ($gD_{1-234}$), 250 ($gD_{1-250}$), 285 ($gD_{1-285}$), or 306 ($gD_{1-306}$).

Examples of live-attenuated or replication-impaired herpesviruses suitable for use include, but are not limited to, Herpes Simplex virus type 1 (HSV-1) or type 2 (HSV-2), VZV, EBV, CMV, HHV-7 and the non-human equine herpesvirus type-1. Such live-attenuated or replication-impaired herpesviruses include: (i) viral vectors (e.g., that consist of a backbone herpesvirus, and in which certain genes have been replaced with that of another virus) and (ii) genetic mutants rendered nonvirulent by the deletion of one or more viral genes but retaining one or more viral glycoproteins. Specific, non-limiting, examples of genetic mutants include replication defective HSV-1 or HSV-2 with mutations in the genes encoding ICP8, UL5 and/or ICP27, the HSV-2 mutant deficient in glycoprotein gH known as DISC (disabled infectious single cycle mutants), and the HSV-2 mutant known as ICP10ΔPK. Examples of replication-defective herpesviruses suitable for use are provided, for example, in U.S. Pat. No. 7,223,411, which is herein incorporated by reference in its entirety.

In certain embodiments, the herpesvirus is the replication-impaired HSV-2 dl5-29 mutant virus (parent strain 186 syn$^+$-1) genetically modified to contain 2 gene deletions: UL5 and UL29 as described in Da Costa, et al (2000) J. Virology 74:7963-7971 and WO 99/06089, the disclosures of which are incorporated by reference in their entireties. The original dl5-29 strain was re-derived and renamed as ACAM529 (Deiagrave S, et al. PLoS ONE, 2012 7(10): e46714). Thus, the terms dl5-29, ACAM529, and HSV-529 may be used interchangeably. The UL5 deletion consists of removal of the UL5 gene and part of the nonessential UL4 open reading frame (ORF) from nucleotides 12,244 to 15,143. The UL5 gene is an essential component of the viral helicase-primase complex and is required for viral DNA synthesis. The UL29 deletion consists of removal of the complete UL29 gene from nucleotides 58,784 to 62,527. The UL29 gene encodes the viral single-stranded DNA binding protein ICP8 (infected cell protein 8), which is essential for viral DNA synthesis. Together, this double mutation results in a virus that only grows on a complementary cell line, AV529-19 Vero cells containing the UL29 and UL5 genes and does not grow on normal Vero cells.

Table 2 shows the sequence of the dl5 deletion site in dl5-29 viral DNA and the sequence of the dl29 deletion site in dl5-29 viral DNA.

| dl5 deletion | ...TCAAAGGGGTACGCG/-/ AAAAACGCCTCG... |
|---|---|
| dl29 deletion | ...GTCACGAGACACGAT/-/ TCGACGGCTGCTGCCCGCCGTCG... |

The live-attenuated or replication-impaired herpesvirus may be cultured on an appropriate cell line (e.g., Vero cells; AV529-19, which is a Vero-based cell line specifically engineered to express the HSV-1 UL5 and UL29 open reading frames) and then purified from the harvested viral culture in one or more steps, A specific example of a cell line suitable for propagating a replication-defective HSV-2 strain is described in U.S. Pat. No. 6,841,373, which is herein incorporated by reference in its entirety.

In certain embodiments, the immunogenic product includes multiple herpesviruses (e.g., two, three or more herpesviruses) which may be of the same or different species. In some embodiments, compositions may comprise one or more virus serotypes (e.g., of HSV-1 and/or HSV-2).

D. FORMULATIONS

In one aspect, this disclosure provides compositions, preferably pharmaceutically acceptable compositions, comprising the immunogenic product and/or anti-herpesvirus antibody described herein.

Pharmaceutical compositions are usually provided in a uniform dosage form and may be prepared in a manner known per se.

In certain embodiment, a pharmaceutical composition is in the form of a solution or suspension. In some such embodiments, the pharmaceutical composition further comprises a pharmaceutically acceptable carrier.

As used herein, "pharmaceutically acceptable carrier" includes any and all solvents, dispersion media, coatings, encapsulating substances, antibacterial and antifungal agents, isotonic and absorption delaying agents, and the like that are physiologically compatible. Suitable pharmaceutically acceptable carriers, particularly for parenteral administration, include, but are not limited to, saline, phosphate buffered saline, dextrose, glycerol, ethanol and the like, as well as combinations thereof.

In certain embodiments, the pharmaceutical composition is an injectable formulation. In some such embodiments, the injectable formulation includes a pharmaceutically acceptable carrier such as Ringer Lactate.

In certain embodiments, the pharmaceutical composition further comprises a buffer and/or preservative, which enhance the shelf life or effectiveness of the antibody. Suitable buffers for use in a pharmaceutical composition include, but are not limited to, acetic acid in a salt, citric acid in a salt, boric acid in a salt and phosphoric acid in a salt. Suitable preservatives for use in a pharmaceutical composition include, but are not limited to, benzalkonium chloride, chlorobutanol, paraben and thimerosal.

In certain embodiments, the pharmaceutical composition further comprises isotonic agents, for example, sugars, polyalcohols such as mannitol or sorbitol.

In certain embodiments, an anti-herpesvirus antibody described herein is incorporated into pharmaceutical compositions suitable for administration to a subject. Typically, the pharmaceutical composition comprises an antibody described herein (such as, for example, an anti-HSV antibody and, in particular, CH42 and/or E317) and a pharmaceutically acceptable carrier.

In some such embodiments, the pharmaceutical composition contains (i) an anti-HSV antibody and (ii) a pharmaceutically acceptable carrier. Such pharmaceutical compositions comprising anti-HSV antibodies described herein are for use in preventing and/or ameliorating the effects of a neonatal HSV infection. In a specific embodiment, a composition comprises a monoclonal anti-HSV antibody described herein. Alternatively, a composition may comprise one or more anti-HSV antibodies described herein (e.g., a polyclonal population of anti-HSV antibodies). In accordance with these embodiments, the composition may further comprise of an additional carrier, a diluent, or an excipient.

In certain embodiments, an immunogenic product comprising a herpesvirus antigen described herein is incorporated into pharmaceutical compositions suitable for administration to a subject. Typically, the pharmaceutical composition comprises an immunogenic product described herein (such as, for example, an replication-impaired HSV and, in particular, dl5-29) and a pharmaceutically acceptable carrier.

In certain embodiments, the herpesvirus antigen is a component in a pharmaceutical composition, such as an anti-herpesvirus vaccine. In some such embodiments, the herpesvirus antigen is an HSV antigen and the vaccine is an anti-HSV vaccine. In some such embodiments, the anti-HSV vaccine comprises an HSV antigen and, optionally, an adjuvant. In certain embodiments, the antigen is glycoprotein D (gD) of HSV or a fragment thereof, such as $gD_{1-306}$. In certain embodiments, the antigen is from a replication defection HSV virus strain, such as an HSV-2 mutant strain containing deletion mutations in the UL29 (ICP8) gene and/or the UL5 gene.

In certain embodiments, a pharmaceutical composition comprising an HSV antigen (i.e., an anti-HSV vaccine) further comprises an adjuvant. Exemplary adjuvants include, but are not limited to oil emulsions (e.g., Freund's adjuvants), mineral compounds (such as alum or other aluminum salts such as aluminum hydroxide, aluminum phosphate, or aluminum sulfate), bacterial products (such as Bordetella pertussis toxin or muramyldipeptide), liposomes, and immune-stimulating complexes. Further examples of adjuvants include, but are not limited to monophosphoryl-lipid-A (MPL SmithKline Beecham), saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol. In some such embodiments, the HSV antigen is present within a nanoemulsion, such as an oil-in-water dispersion or droplet or a lipid structure such as unilamellar, paucilamellar, and multilamellar lipid vesicles, micelles, and lamellar phases. Nanoemulsion particle size may be from 300 to 600 nanometers.

In certain embodiments for any of the aspects described herein, the immunogenic product and/or anti-herpesvirus antibody is administered with one or more additional agents, e.g., a therapeutic agent (for example, a small molecule or biologic), said additional agent being selected by the skilled artisan for its intended purpose. For example, in one embodiment, an anti-HSV antibody is administered with an antiviral agent, particularly an anti-HSV agent such as acyclovir. Thus, in a further embodiment, a pharmaceutical composition disclosed herein may comprise at least one additional therapeutic agent for treating or preventing a viral infection

E. ADMINISTRATION

In one aspect, this disclosure provides methods in which the immunogenic product and/or anti-herpesvirus antibody described herein is administered to a subject.

In certain embodiments, the subject is a maternal subject. In some such embodiments, the maternal subject is pregnant or likely to become pregnant. In certain embodiments, the subject is a neonate (e.g., a human infant less than four weeks old).

In certain embodiments, the subject is a neonatal subject. In some such embodiments, the neonatal subject is infected with a herpesvirus. In other such embodiments, the neonatal subject is at risk of being infected with a herpesvirus. Subjects at risk for being infected with a herpesvirus include patients who have come into contact with an infected person or who have been exposed to HSV in some other way. Prophylactic administration can occur prior to the manifestation of symptoms characteristic of a herpesvirus infection, such that infection is prevented or, alternatively, its severity and/or the neurological or behavioral consequences thereof are lessened.

The immunogenic product and/or anti-herpesvirus antibody, and, more particularly, pharmaceutical compositions comprising the immunogenic product and/or anti-herpesvirus antibody, may be administered via any conventional route, such as by parenteral administration including by injection or infusion. Administration is preferably parenterally, such as intravenously, subcutaneously, intradermally or intramuscularly.

Compositions suitable for parenteral administration, which are discussed herein in further detail, typically will comprise a sterile aqueous or nonaqueous preparation, which is preferably isotonic to the blood of the recipient. Examples of compatible carriers and solvents are Ringer solution and isotonic sodium chloride solution. In addition, usually sterile, fixed oils are used as solution or suspension medium.

In certain embodiments, an anti-HSV antibody (or a nucleic acid and/or vector encoding the anti-HSV antibody) is a component in a pharmaceutical composition. In certain embodiments, the pharmaceutical composition comprising the antibody is administered parenterally. In certain embodiments, the pharmaceutical composition comprising the antibody is administered intravenously or intramuscularly. In certain embodiments, the pharmaceutical composition comprising the antibody is administered subcutaneously or intradermally.

In certain embodiments, the anti-HSV antibody is systemically administered to subject, such as by intravenous injection. Alternatively or additionally, the anti-HSV antibody may be delivered to the maternal subject via vector-mediated delivery (e.g., a nucleic acid encoding the antibody is administered to the maternal subject).

In certain embodiments, an immunogenic product is a component in a pharmaceutical composition, such as a vaccine. In certain embodiments, the vaccine is administered orally. In certain embodiments, the vaccine is administered parenterally. In some such embodiments, the vaccine is administered topically, intravenously, subcutaneously, intraperitoneally, intranasally, or intramuscularly. In certain embodiments, the vaccine is administered subcutaneously, intradermally, or intramuscularly.

In certain embodiments, the immunogenic product is administered to a subject once. Alternatively, in certain embodiments, the immunogenic product is administered to the subject repeatedly. In some such embodiments, the repeated administration occurs at in regular intervals, such as once every 21 days, once every month, once every two months, or the like. In certain embodiments, a first dose of an immunogenic product is administered to the subject at a first time (e.g., day 0) and a subsequent dose of an immunogenic product is administered to the subject at a subsequent time (e.g., day 21). In some such embodiments, the first and second doses comprise the same immunogenic product. In other such embodiments, the first and second doses comprise different (but antigenically overlapping) immunogenic products.

In certain embodiments, the immunogenic product, and more particularly, a pharmaceutical composition comprising the immunogenic product (e.g., a vaccine), is administered with an immunostimulatory cytokine. Exemplary immunostimulatory cytokines include but are not limited to granulocyte-macrophage colony stimulating factor (GM-CSF), interleukin 1, interleukin 2, interleukin 12, interleukin 18, or interferon-gamma.

In certain embodiments, the immunogenic product, and more particularly, a pharmaceutical composition comprising the immunogenic product (e.g., a vaccine), is administered with an adjuvant. Exemplary adjuvants are described herein and include, but are not limited to oil emulsions (e.g., Freund's adjuvants), mineral compounds (such as alum or other aluminum salts such as aluminum hydroxide, aluminum phosphate, or aluminum sulfate), bacterial products (such as Bordetella pertussis toxin), liposomes, and immune-stimulating complexes.

The biological compositions described herein are administered in effective amounts. An "effective amount" refers to the amount which achieves a desired effect alone or together with further doses. In certain cases, the desired effect includes reduction and/or prevention of a particular outcome, such as neonatal herpesvirus infection and/or the neurological and/or behavioural consequences thereof. In certain cases, the desired effect includes achieving a neutralizing anti-herpesvirus antibody titer in serum (or other bodily fluid relevant to a target site).

An effective amount of an agent or composition described herein will depend on the particular infection(s) to be treated and/or prevented, the severeness of the underlying infection (if any), the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

In certain embodiments for any of the aspects described herein, the immunogenic product and/or anti-herpesvirus antibody is administered with one or more additional agents, e.g., a therapeutic agent (for example, a small molecule or biologic), said additional agent being selected by the skilled artisan for its intended purpose. For example, in one embodiment, an anti-HSV antibody is administered with an antiviral agent, particularly an anti-HSV agent such as acyclovir. Thus, in a further embodiment, a method further comprises co-administration of at least one additional therapeutic agent for treating or preventing a viral infection.

F. SPECIFIC EMBODIMENTS (A1) A method for preventing or ameliorating the effects of a neonatal herpes simplex virus (HSV) infection comprising: administering to a maternal subject (i) an HSV antigen and/or (ii) an anti-HSV antibody.

(A2) The method of embodiment A1, wherein the anti-HSV antibody specifically binds to glycoprotein D of HSV and, preferably, is a neutralizing antibody.

(A3) The method of embodiment A1, wherein the anti-HSV antibody blocks interaction between glycoprotein D and herpesvirus entry mediator (HVEM).

(A4) The method of embodiment A1, wherein the anti-HSV antibody has the binding specificity of mAb 5188.

(A5) The method of embodiment A1, wherein the anti-HSV antibody comprises
a heavy chain variable region ($V_H$) having
    a $V_H$ CDR1 having an amino acid sequence of SEQ ID NO: 1,
    a $V_H$ CDR2 having an amino acid sequence of SEQ ID NO: 2, and
    a $V_H$ CDR3 having an amino acid sequence of SEQ ID NO: 3; and
a light chain variable region ($V_L$) having
    a $V_L$ CDR1 having an amino acid sequence of SEQ ID NO: 4,
    a $V_L$ CDR2 having an amino acid sequence of SEQ ID NO: 5, and
    a $V_L$ CDR3 having an amino acid sequence of SEQ ID NO: 6.

(A6) The method of embodiment A1, wherein the anti-HSV antibody comprises a heavy chain variable region (VH) having an amino acid sequence of SEQ ID NO: 7 and a light chain variable region (VL) having an amino acid sequence of SEQ ID NO: 8.

(A7) The method of embodiment A1, wherein the HSV antigen is glycoprotein D of HSV or a fragment thereof.

(A8) The method of any of the preceding embodiments, wherein the maternal subject is HSV seronegative.

(A9) The method of any of the preceding embodiments, wherein the maternal subject is suspected of having a primary HSV infection.

(A10) The method of any of the preceding embodiments, wherein the maternal subject is pregnant.

(A11) The method of any of the preceding embodiments, wherein the HSV antigen and/or anti-HSV antibody is administered to the maternal subject prior to parturition.

(B1) A method for treating or preventing or treating a neonatal herpes simplex virus (HSV) infection and/or neurological or behavioral consequences thereof comprising: (a) identifying a neonatal patient in need of such treatment or prevention, and (b) administering to said patient an effective amount of at least one anti-HSV antibody.

(B2) The method of embodiment B1, wherein the neonatal patient is infected with HSV.

(B3) The method of embodiment B1, wherein the neonatal patient is at risk for being infected with HSV.

(B4) The method of embodiment B1, wherein the neonatal patient has been exposed to HSV.

It will be readily apparent to those skilled in the art that other suitable modifications and adaptations of the compositions and methods of the invention described herein may be made using suitable equivalents without departing from the scope of the invention or the embodiments disclosed herein.

The compounds, compositions, and methods described herein will be better understood by reference to the following examples, which are included as an illustration of and not a limitation upon the scope of the invention.

G. EXAMPLES

Example 1: Prophylactic/Maternal Treatment with Anti-HSV Antibody

Monoclonal antibody CH42 or a control antibody (VRC01, a broadly neutralizing HIV-specific antibody) was administered to female mice (dams) prior to or during pregnancy. Pups were challenged 1-2 days post-partum with HSV. In vivo bioluminescent imaging was used to track the progression of nHSV.

Figure 1B:
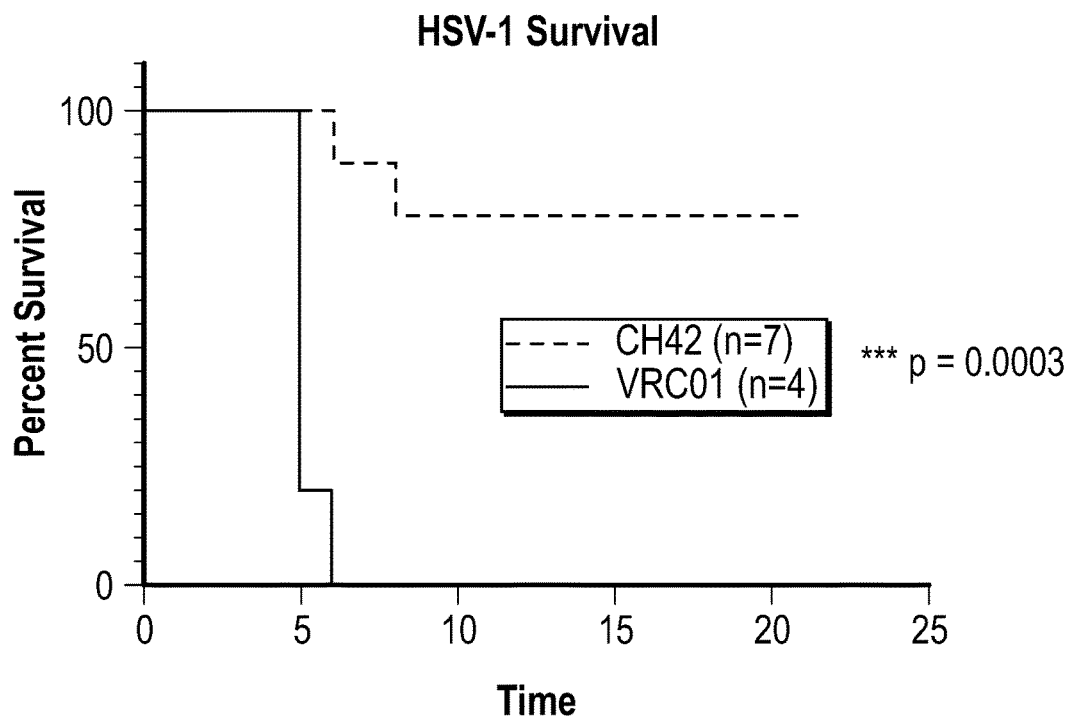
FIG. 1B is a HSV-1 survival plot showing survival of pups from dams treated with CH42 or VRC01. Naïve pregnant dams were treated with 500 ug of CH42 or VRC-01 3 days prior to parturition. Pups were infected with 10,000 pfu of HSV-1 strain 17 WT.

Maternal administration of CH42 was protective against nHSV associated neurological disease and death (FIGS. 1A and 1B). Treatment of dams with CH42 increased survival of lethal HSV-1 challenge.

Figure 1C:
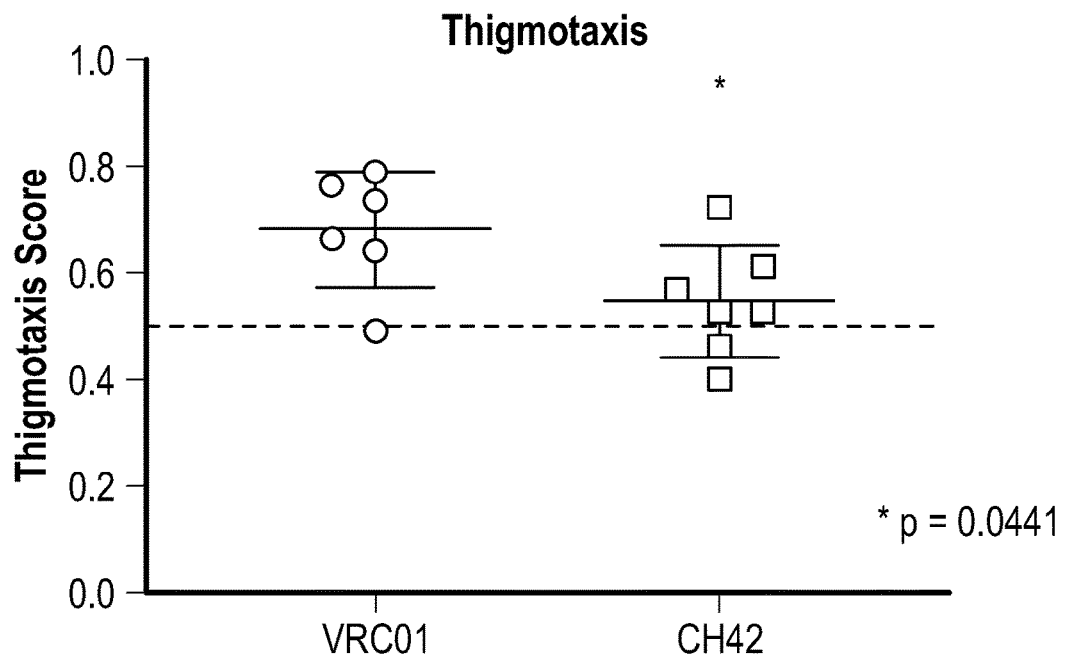
FIG. 1C is a plot showing quantification of thigmotaxis, a ratio of time spent in the outer perimeter over time, for offspring of CH42 or VRC01 control treated dams.

Offspring were examined for behavioral changes using a mouse model of the neurodevelopmental defects/neurological morbidity seen in surviving nHSV patients by measuring a behavior known as thigmotaxis, an anxiety-like activity in the mice. CH42 administration to dams completely prevented thigmotaxis in their HSV-infected offspring (FIG. 1C). Thus, maternal administration of CH42 provided protection not only at the level of mortality, but also morbidity in the form of preventing behavioral sequelae, including anxiety-like behavior.

Maternal administration of a neutralizing anti-HSV antibody can be a therapeutic approach to preventing nHSV infection, reducing mortality, and combating neurological sequelae in nHSV survivors.

Example 2: Day of Infection Treatment with Anti-HSV Antibody

P2 pups from untreated dams were intranasally challenged with HSV-1 strain 17 expressing luciferase (st17dlux). On the same day, monoclonal antibody CH42 (40 µg) or a control antibody (VRC01) was administered directly to st17dlux-infected pups via intraperitoneal injection. The pups were then monitored for weight change, progression of infection, viral titers, and survival.

Figure 2A:
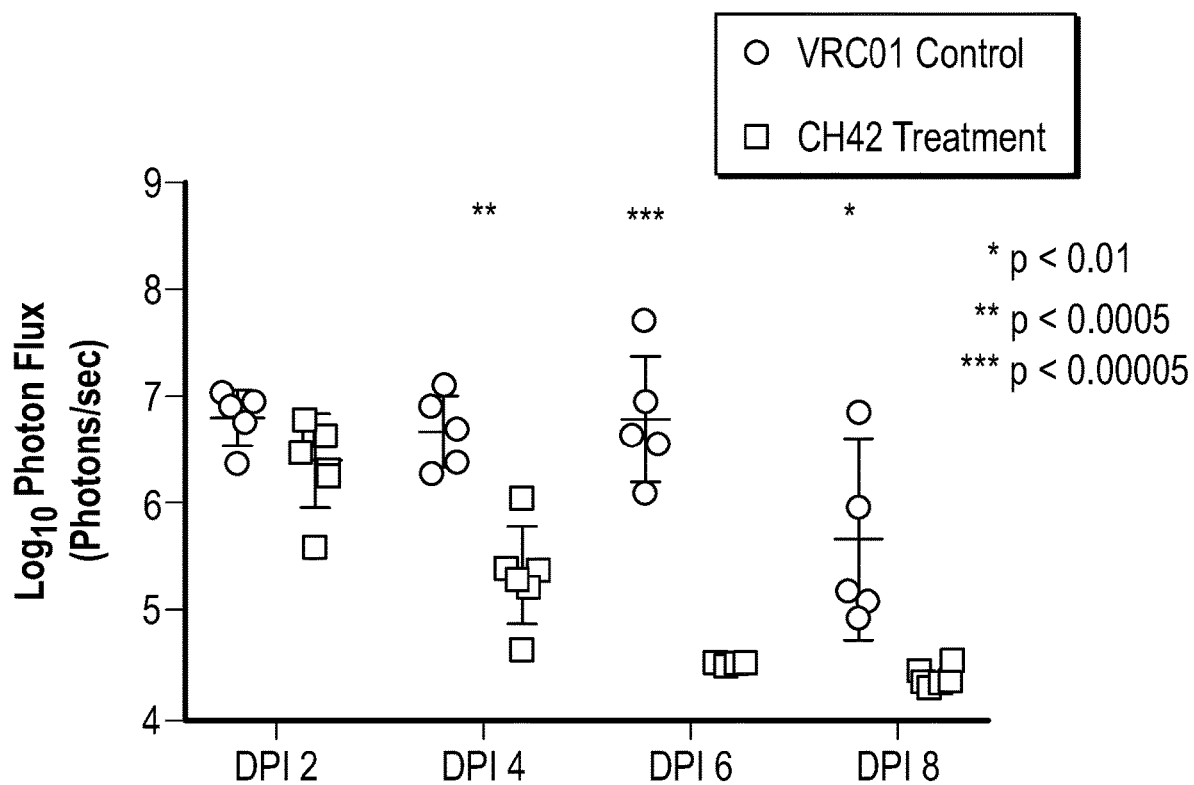
FIG. 2A is a plot showing quantification of total luminescence on pups challenged with HSV-1 st 17 expressing luciferase (st17dlux). Pups from untreated dams were administered an anti-HSV antibody (CH42) or a control antibody (VRC01) on the day of infection.
Figure 2B:
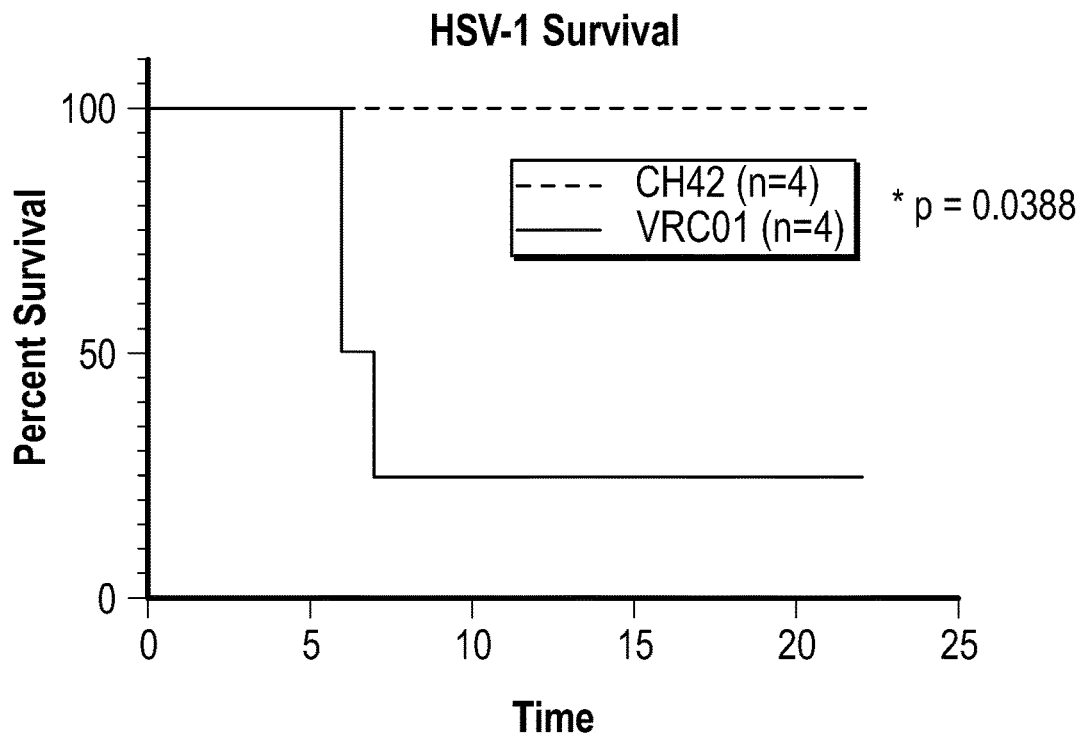
FIG. 2B is a HSV-1 survival plot showing survival of pups from untreated dams. Pups were treated with CH42 or VRC01 and then immediately infected with 1,000 pfu of HSV-1 strain 17 WT.

Direct administration of the antibody on the day of infection protected pups from HSV-1 neurological disease and conferred a survival benefit. (FIG. 2A, 2B).

Example 3: Post-Infection Treatment with Anti-HSV Antibody

P2 pups from untreated dams were intranasally challenged with HSV-1 strain 17 expressing luciferase (st17dlux). One day post-infection, monoclonal antibody CH42 or a control antibody (VRC01) was administered directly to st17dlux-infected pups via intraperitoneal injection.

Figure 3:
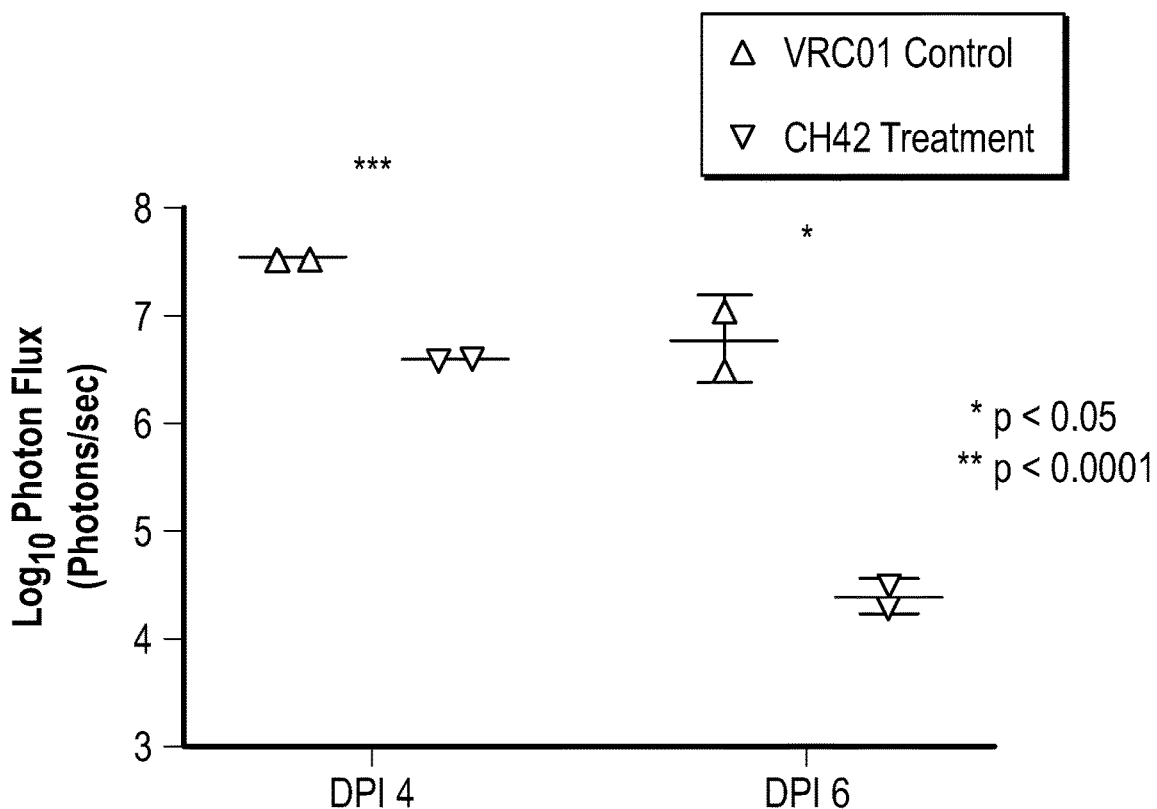
FIG. 3 is a plot showing quantification of total luminescence on pups challenged with HSV-1 st 17 expressing luciferase (st17dlux). Pups from untreated dams were administered an anti-HSV antibody (CH42) or a control antibody (VRC01) 1 day post-infection.

Direct administration of the antibody one day post-infection protected pups from HSV-1 neurological disease. (FIG. 3).

Example 4: Prophylactic/Neonatal Treatment with Anti-HSV Antibody

Pups from untreated dams were treated with 10 µg of mAb E317. One day after treatment, pups were challenged with 1,000 pfu HSV-1 strain 17 WT.

Figure 4:
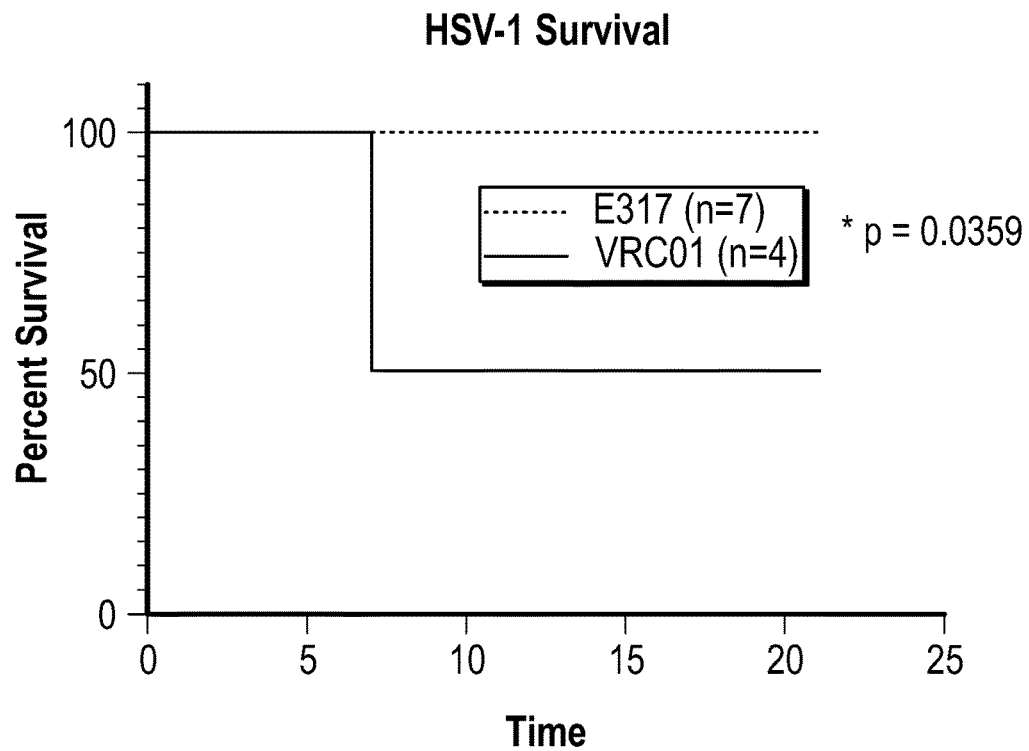
FIG. 4 is a HSV-1 survival plot showing survival of pups from untreated dams administered an anti-HSV-1 antibody (E317) or a control antibody (VRC01) 1 day pre-infection.

Direct administration of the antibody one day pre-infection conferred 100% survival of pups challenged with HSV-1. (FIG. 4).

Example 5: Antibody Expression System

Cloning techniques by Balazs et. al (Nature, 2012) were utilized to develop an in vivo monoclonal antibody expression system, which allows for long lasting antibody expression. Briefly, construction of an adeno associated virus (AAV) vector included 2 inverted terminal repeat sequences which flanked a CASI promoter, followed by the genetic sequence required to generate the gene of interest (Ig heavy and light chain joined together by a 2A self-cleaving peptide linker), an enhancer sequence (WPRE), and a polyadenylation signal (SV40). Constructs for CH42, E317, and an isotype control antibody were delivered via intramuscular injection at a dose of $1\times10^{11}$ to female mice. Eight weeks were allowed to pass to reach stable expression of the antibodies. The dams were bred and their progeny challenged with HSV-1. An HSV-1 dose of 1,000 pfu was used to assess survival, and a dose of 100 pfu was used to assess neurological damage. The results of these experiments yielded similar results to those reported herein, indicating that a long lasting in vivo delivery system conferred protection from neonatal HSV.

Example 6: Prophylactic/Maternal Treatment with HSV Vaccine

This study was designed to determine whether maternal vaccination could provide sufficient antibody to offspring and whether this could ultimately protect against neonatal herpes. Mouse studies were conducted using litters from six to eight different dams per group.

Eight-week old B6 female mice were immunized twice intramuscularly with $10^5$ PFU of extracellular dl5-29 virus, mock cell lysate, or PBS in a 25 µl volume. Injections were carried out 21 days apart and while mice were under isoflurane anesthesia. HSV-2 dl5-29 is a replication-defective virus that lacks the genes for the UL5 helicase-primase subunit and the UL29 (ICP8) DNA binding protein and was derived from HSV-2 186 syn+. See Costa X, et al., J. Virol. 74, 7963-7971 (2000), which is herein incorporated by reference in its entirety.

Maternal Transfer of HSV-Specific Antibodies.

Figure 5A:
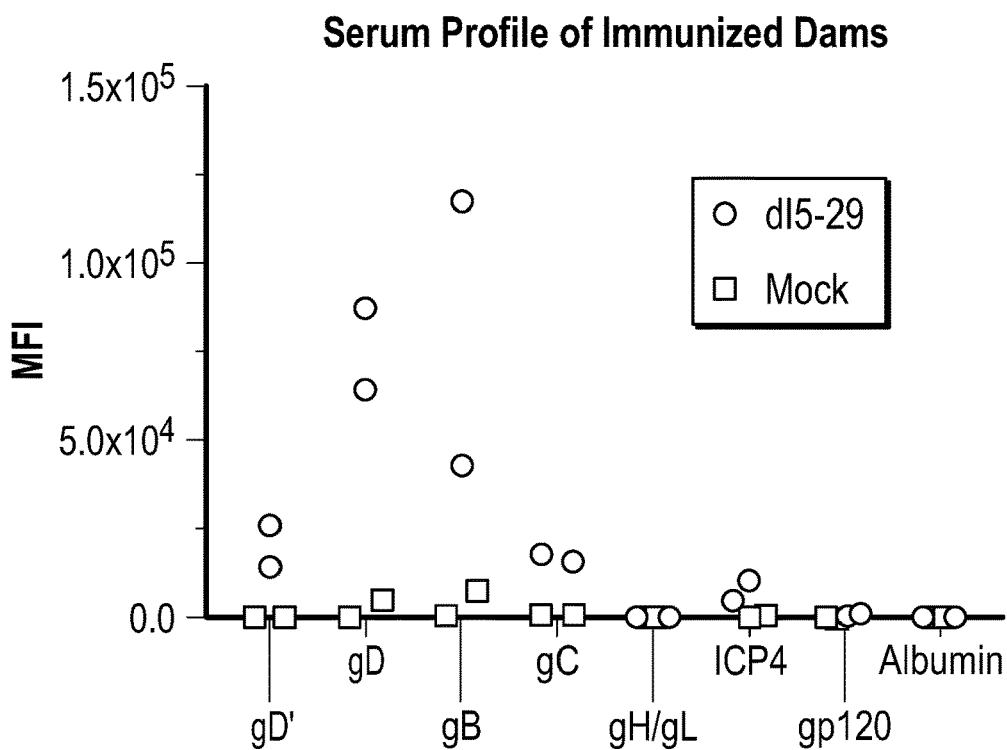
FIG. 5A is a plot showing median fluorescence intensity (MFI) for various proteins from sera from immunized dams (gD' refers to the ectodomain of HSV-1 gD).
Figure 5B:
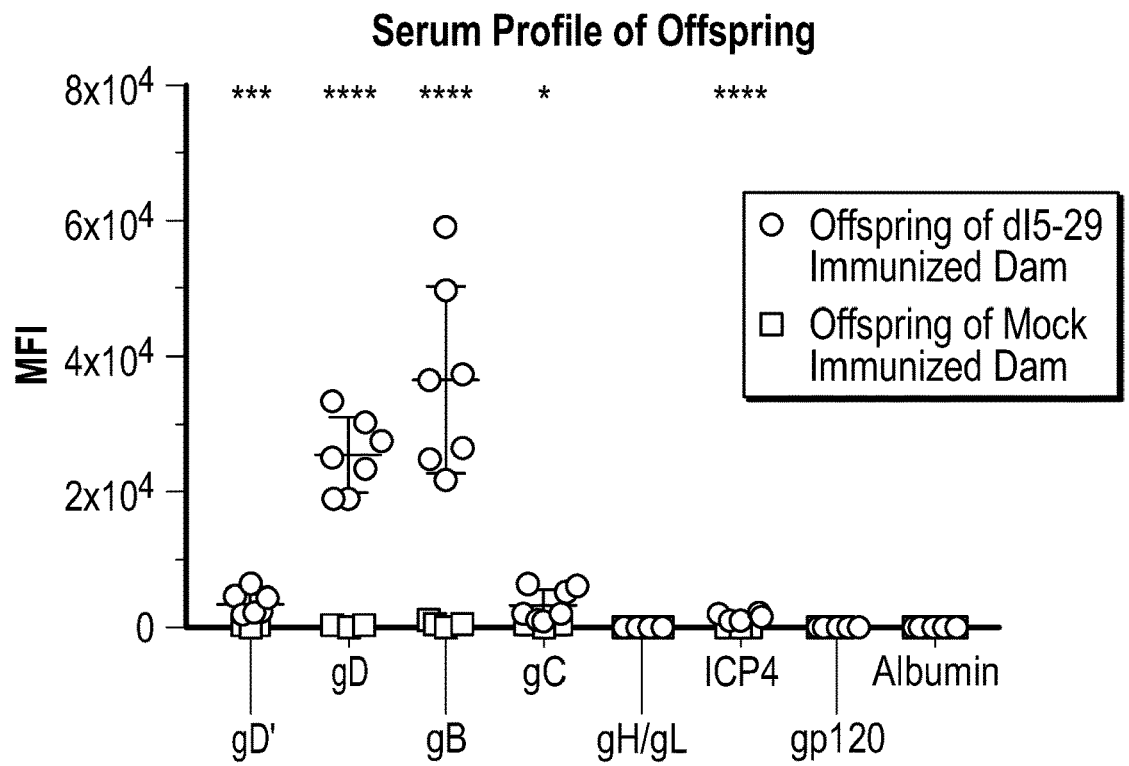
FIG. 5B is a plot showing median fluorescence intensity (MFI) for various proteins from sera from offspring of immunized dams (gD' refers to the ectodomain of HSV-1 gD).
Figure 5C:
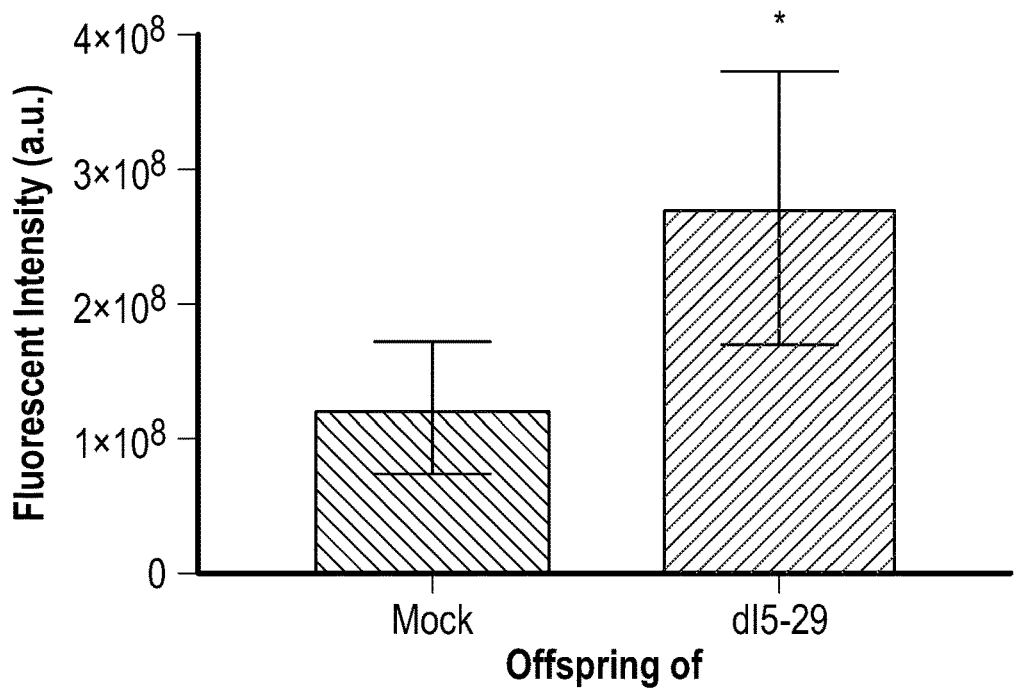
FIG. 5C is a bar graph showing fluorescence intensity (a.u.=arbitrary units) of anti-mouse IgG in trigeminal ganglia (TG) tissue sections.

To determine whether IgG antibodies resulting from immunization could access the neonatal circulation, the presence and quantities of HSV-specific antibody in serum of paired dams and pups was assessed. Immunized dams produce antibodies specific for gD, gC, gB, and ICP4 (FIG. 5A). Likewise, serum from the offspring of the dl5-29-immunized group had significantly increased antibody binding to gD, gC, gB, and ICP4 relative to offspring of mock-immunized dams (P=0.0005, 0.0102, 0.00001, and 0.00002) (FIG. 5B). To determine whether IgG antibodies could access the neonatal nervous system, the trigeminal ganglia (TG) of uninfected pups from dl5-29- and mock-immunized dams were compared using immunofluorescence microscopy. The data showed elevated staining for mouse IgG in the TGs from the immunized group (FIG. 5C). Together, these results indicate that dams mounted an antibody response after immunization that can be transferred to the circulation and nervous systems of their offspring.

Maternal Immunization Protected Against Neonatal Herpes.

To determine whether immunization was sufficient to protect against nHSV, pups were challenged intranasally with lethal doses of HSV-1. Viral titers and survival were measured.

Figure 6A:
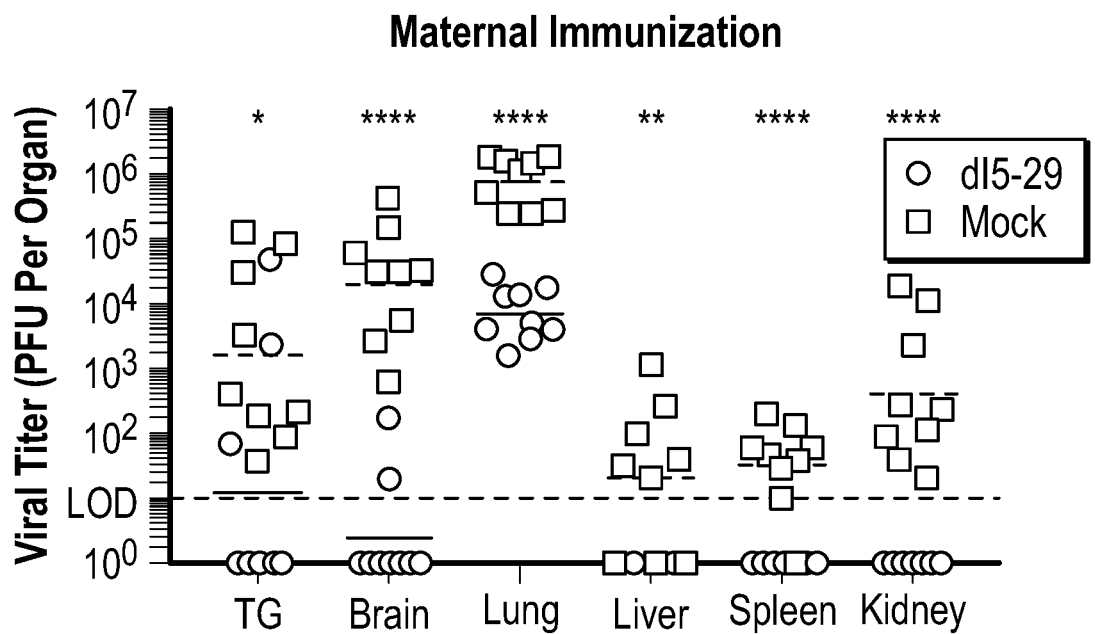
FIG. 6A is a plot showing viral titers in perfused organs from neonates from dl5-29- or mock-immunized dams. Pups were infected with $10^4$ PFU of HSV-1.
Figure 6B:
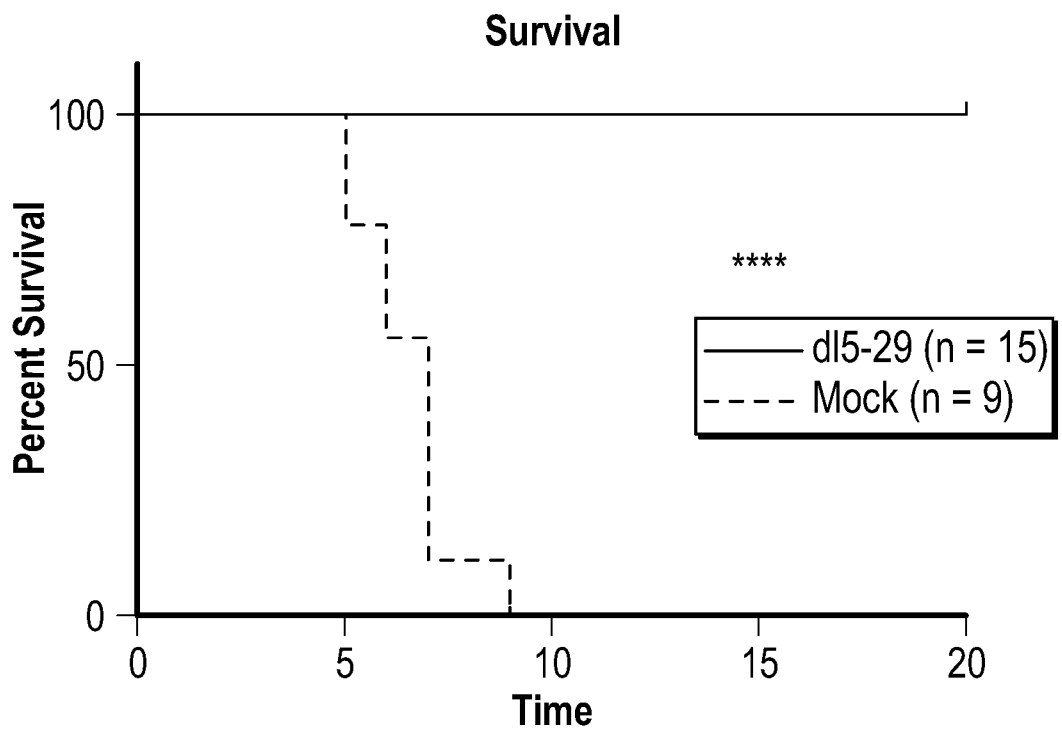
FIG. 6B is a HSV-1 survival plot showing survival of neonates from dl5-29- or mock-immunized dams. Pups were challenged with $10^3$ PFU of HSV-1.

Pups of dl5-29-immunized dams showed significantly decreased viral burden in the CNS (P<0.000001) and peripheral nervous system (P=0.0121) and in various visceral organs (P<0.003) (FIG. 6A). These pups survived the HSV challenge, whereas pups of mock-immunized dams succumbed to infection (FIG. 6B).

Figure 6C:
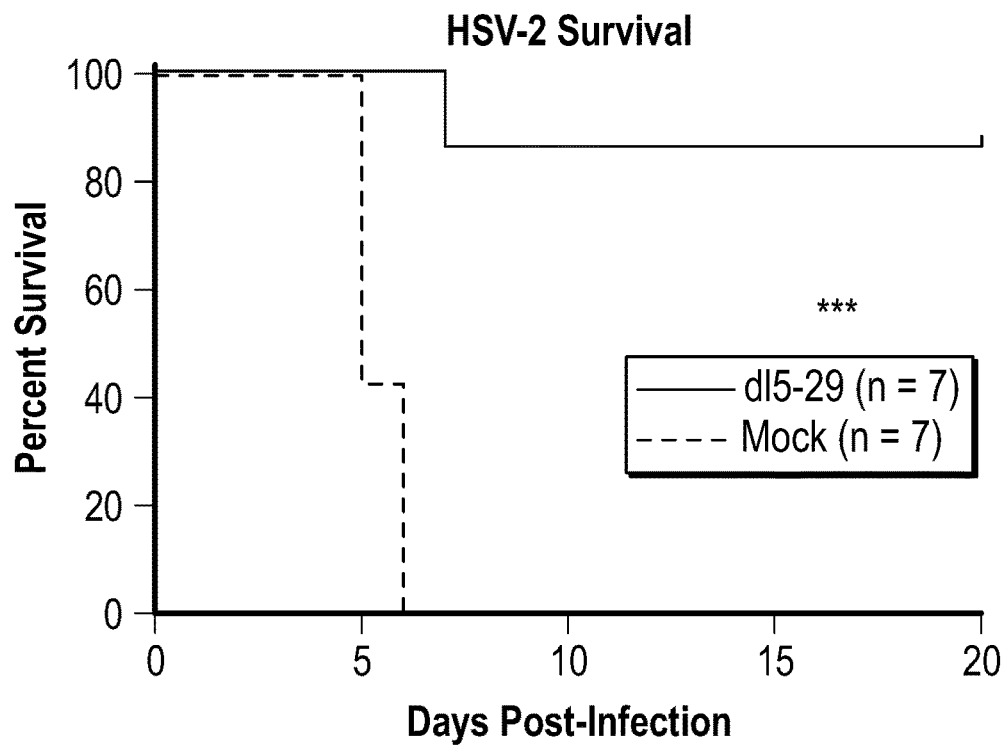
FIG. 6C is a HSV-2 survival plot showing survival of neonates from dl5-29- or mock-immunized dams. Pups were challenged with $10^3$ PFU of HSV-2.
Figure 6D:
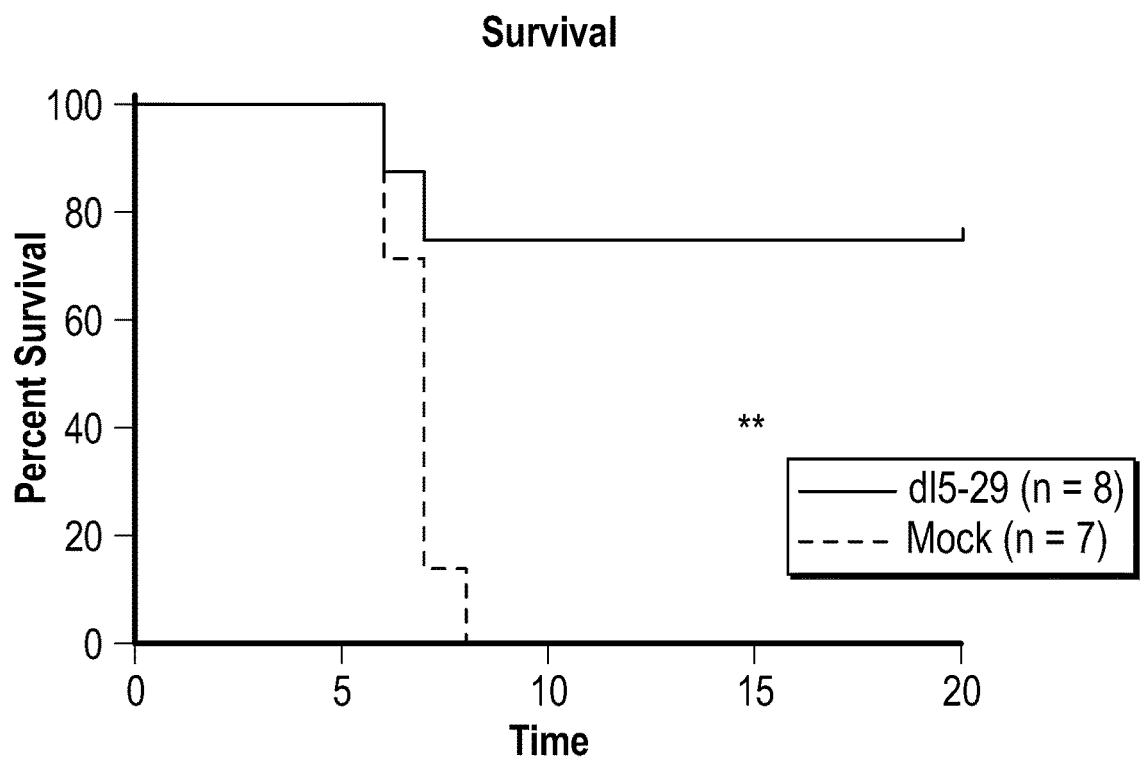
FIG. 6D is a survival plot showing survival of offspring of dl5-29- or mock-immunized dams following 5 pregnancies (245 days post-immunization). Pups were challenged with $10^3$ PFU of HSV-1.

Offspring of immunized dams were also challenged with a heterologous and low-passage clinical HSV-2 isolate (strain G). Comparable protection was found (FIG. 6C). Protection extended to at least four subsequent pregnancies (≥245 days) from these dams, demonstrating that the antibody response was long-lasting and provides protective immunity against nHSV (FIG. 6D).

Figure 6E:
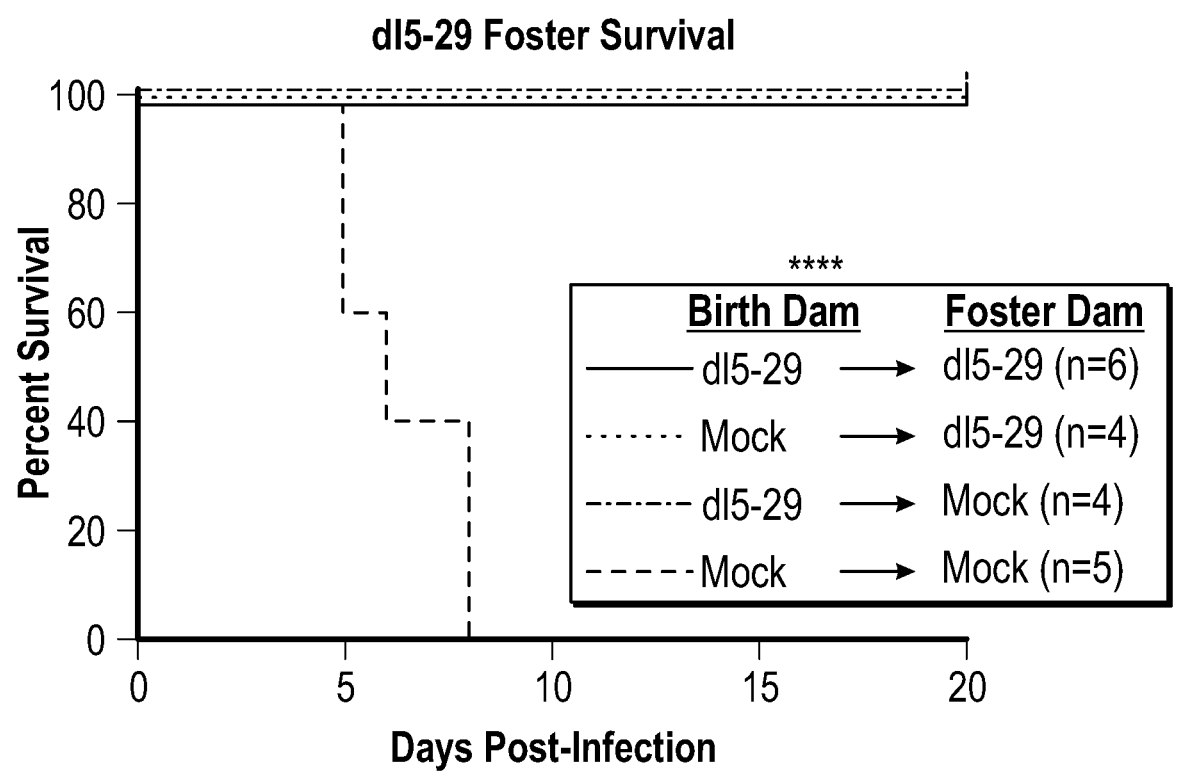
FIG. 6E is a survival plot showing survival of neonates as a function of foster dam to assess milk and placental protective contributions.

Humans and mice both transfer immunoglobulins vertically via placental transfer to the fetus, but mice additionally pass mammary antibody secretions to suckling offspring before gut closure. To address this difference, and to separate the relative contributions of placenta- and milk-derived antibodies to protection, fostering techniques were used. Offspring from mock- or dl5-29-immunized dams were removed immediately at birth from their birth dam and fostered by equivalent or reciprocal (mock- or dl5-29-immunized) dams before being challenged with HSV-1. Equivalent survival was observed between litters that received immunization-derived antibodies via the placenta only or milk only (FIG. 6E). Thus, maternal vaccination with dl5-29 was protective against both HSV-1 and a heterologous HSV-2 strain, and antibody transferred via the placenta was sufficient to completely protect offspring.

Maternal Immunization Prevented Anxiogenic Behavior Caused by Neonatal Herpes.

Even with antiviral treatment, infants that survive nHSV infection of the CNS are left with lifelong debilitating neurological impairments. The open field test (OFT), a behavioral assay that measures general ambulatory ability, novel environment exploration, and anxiety in rodents was used as a model system for monitoring these neurological sequelae. See Simon P, et al., Behav. Brain Res. 61, 59-64 (1994) and Seibenhener M L, et al., J. Vis. Exp, e52434 (2015). When mice are introduced into a novel environment, they demonstrate exploratory behavior. Thigmotaxis, a tendency to remain close to the periphery of an enclosure, is indicative of anxiety-like behavior in both mice and humans.

Figure 7A:
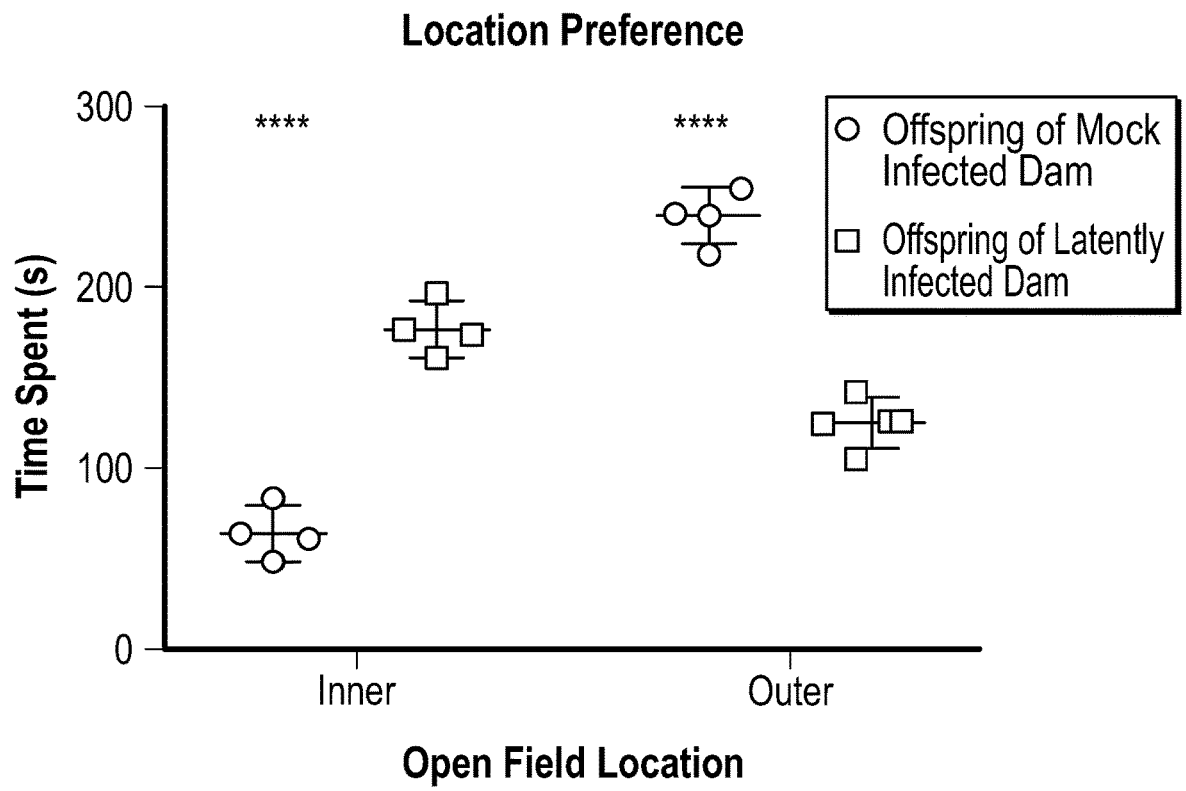
FIG. 7A is a plot showing quantification of location preferences as time spend in the inner region and outer periphery for offspring of latently infected or mock infected dams. Pups were challenged with 100 PFU HSV-1 and were analyzed in the Open Field Test (OFT) at 5 weeks post-infection.
Figure 7B:
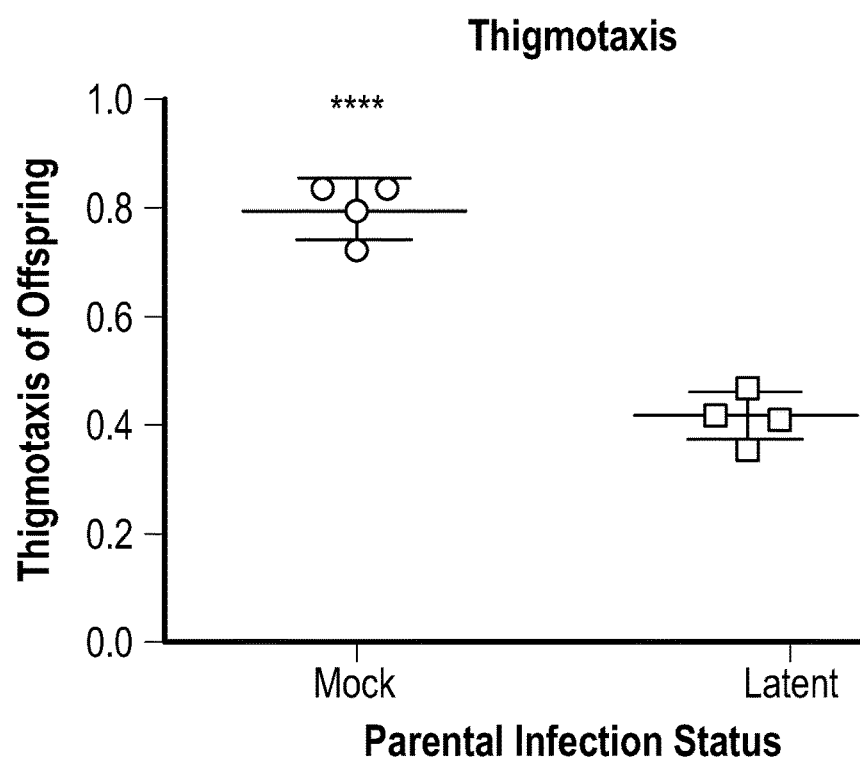
FIG. 7B is a plot showing quantification of thigmotaxis, a ratio of time spent in the outer perimeter over time for offspring of latently infected or mock infected dams.

Offspring (P1-2) of latently infected and mock-infected dams were challenged with a low dose (100 PFU) of HSV-1 and monitored until 5 weeks of age. A low dose was used to ensure survival of both cohorts, and at this dose, no differences in mortality, weight, water consumption, or motor function were observed. However, the OFT revealed that offspring of mock-infected dams had an affinity for the periphery and corners of the test arena, thus demonstrating elevated thigmotaxis; offspring of latently infected dams, conversely, spent similar amounts of time exploring the outer and central areas (FIGS. 7A & 7B).

Figure 7C:
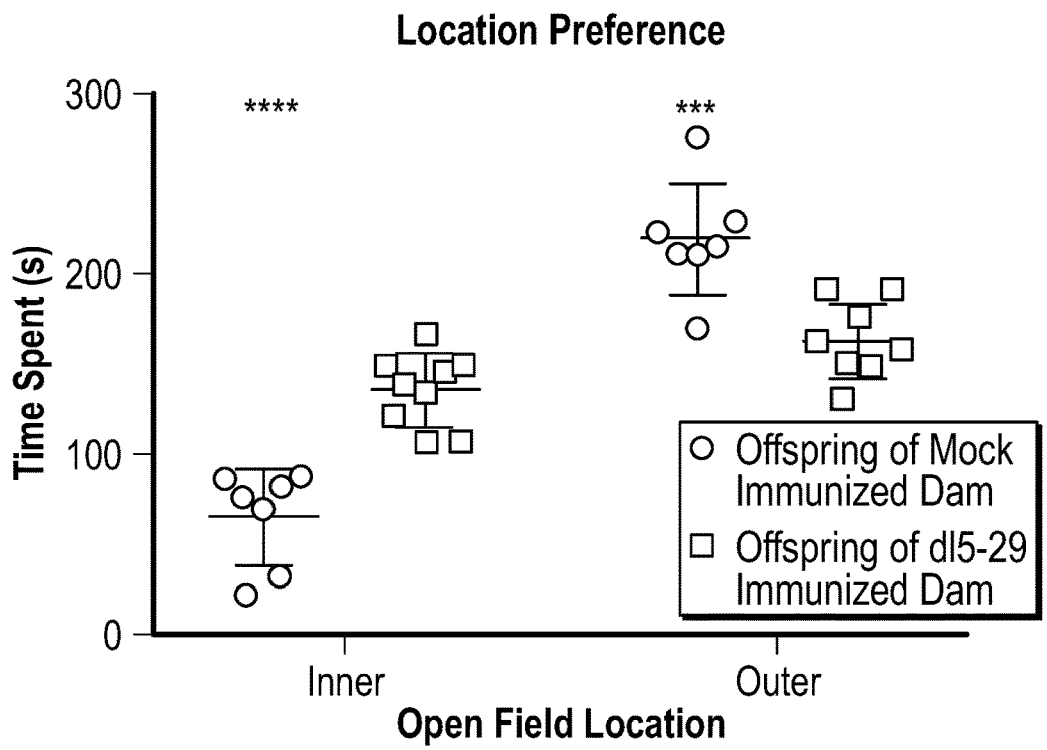
FIG. 7C is a plot showing quantification of location preferences as time spend in the inner region and outer periphery for offspring of dl5-29- or mock-immunized dams. Pups were challenged with 100 PFU HSV-1 and were analyzed in the OFT at 5 weeks post-infection.
Figure 7D:
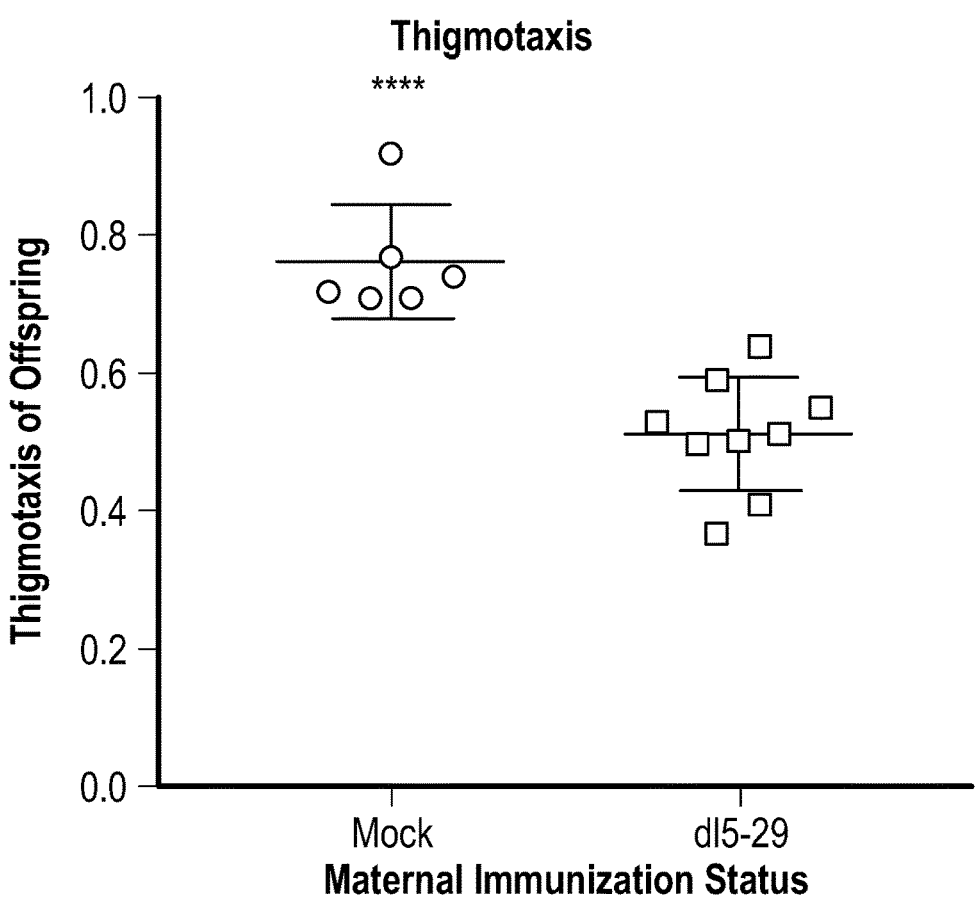
FIG. 7D is a plot showing quantification of thigmotaxis, a ratio of time spent in the outer perimeter over time for offspring of dl5-29- or mock-immunized dams.
Figure 7E:
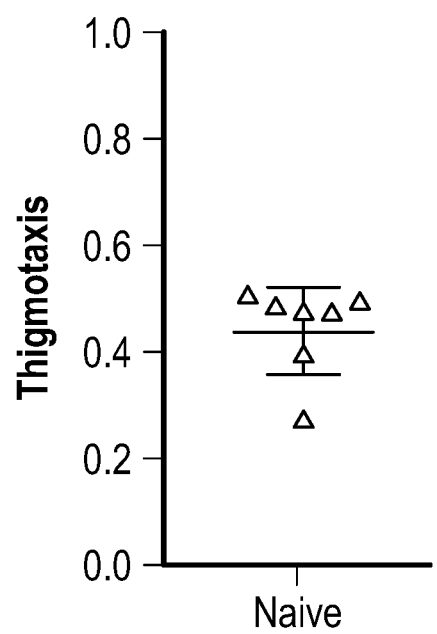
FIG. 7E is a plot showing thigmotaxis of age-matched naïve control mice.

To assess whether maternal immunization could prevent this anxiety-like behavior in offspring challenged with HSV, offspring from dl5-29- and mock-immunized dams were challenged with a low dose of HSV-1. Offspring of mock-immunized females exhibited increased thigmotaxis regardless of distance traveled in the OFT; offspring of dl5-29-immunized dams displayed normal thigmotaxis and their behavior was comparable to naïve, age-matched controls (FIG. 7C, 7D, 7E).

These findings suggest that even low dose and sublethal neonatal infection with HSV-1 can result in behavioral morbidity, and this morbidity is preventable by maternal immunity or immunization.

These findings demonstrate that neonatal exposure to sub-lethal doses of HSV can cause behavioral changes that model neurological morbidities in humans. Infection with pathogens that can cause neurological complications, including *Toxoplasma gondii*, group B streptococcus, malaria, Zika virus, and dengue virus, induces cognitive behavioral changes in rodent models. Infection triggers pro-inflammatory cytokines and microglial activation in the brain and can impact mood, cognition, and behavior.

These findings confirm that the maternal virome is likely an important determinant of health and suggest that permanent behavioral changes may be caused by nHSV in babies born to mothers without preexisting immunity. As such, the timely acquisition of immunity to a pathogen can lead to considerable benefits for the offspring. Thus, in addition to standard infection outcomes, immunization efficacy can be measured against other medical outcomes, such as behavioral pathologies and age-dependent cognitive decline.

Without wishing to be bound by theory, antibody access to fetal neural tissue may prevent infection by other vertically transmitted pathogens. For example, the TORCH pathogens (*Toxoplasma*, other, rubella, cytomegalovirus, and HSV) and Zika virus can cause severe neurological sequelae in fetuses and neonates. Active or passive immunization may mitigate disease in this at-risk population.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A method for protecting offspring against neurological or behavioral consequences of neonatal herpes simplex virus (HSV) infection, the method comprising:
   administering to a maternal subject an anti-HSV antibody, wherein the maternal subject is HSV seronegative and the maternal subject is pregnant.

2. The method of claim 1, wherein the anti-HSV antibody comprises:
   (i) a heavy chain variable region (VH) having
      a $V_H$ CDR1 having an amino acid sequence of SEQ ID NO: 1,
      a $V_H$ CDR2 having an amino acid sequence of SEQ ID NO: 2, and
      a $V_H$ CDR3 having an amino acid sequence of SEQ ID NO: 3; and
   (ii) a light chain variable region (VL) having
      a $V_L$ CDR1 having an amino acid sequence of SEQ ID NO: 4,
      a $V_L$ CDR2 having an amino acid sequence of SEQ ID NO: 5, and
      a $V_L$ CDR3 having an amino acid sequence of SEQ ID NO: 6.

3. The method of claim 1, wherein the anti-HSV antibody comprises a heavy chain variable region (VH) having an amino acid sequence of SEQ ID NO: 7 and a light chain variable region (VL) having an amino acid sequence of SEQ ID NO: 8.

4. The method of claim 1, wherein the anti-HSV antibody comprises:
   (i) a heavy chain variable region ($V_H$) having
      a $V_H$ CDR1 having an amino acid sequence of SEQ ID NO: 10,
      a $V_H$ CDR2 having an amino acid sequence of SEQ ID NO: 11, and
      a $V_H$ CDR3 having an amino acid sequence of SEQ ID NO: 12; and
   (ii) a light chain variable region ($V_L$) having
      a $V_L$ CDR1 having an amino acid sequence of SEQ ID NO: 13,
      a $V_L$ CDR2 having an amino acid sequence of SEQ ID NO: 14, and
      a $V_L$ CDR3 having an amino acid sequence of SEQ ID NO: 15.

5. The method of claim 1, wherein the anti-HSV antibody comprises a heavy chain variable region (VH) having an amino acid sequence of SEQ ID NO: 16 and a light chain variable region (VL) having an amino acid sequence of SEQ ID NO: 17.

6. The method of claim 1, wherein the neurological or behavioral consequences include an anxiety or mood disorder, such as generalized anxiety disorder, acute anxiety disorder, post-traumatic stress disorder (PTSD), phobias, panic disorder, major depressive disorder, bipolar illness, obsessive-compulsive disorder, and somatization disorder, or cognitive decline.

7. The method of claim 1, wherein the anti-HSV antibody is administered to the maternal subject via vector-mediated delivery.

8. The method of claim 7, wherein the vector-mediated delivery is AAV vector-mediated delivery.

9. The method of claim 1, wherein the neurological or behavioral consequences is an anxiety disorder.

10. A method for protecting offspring against neurological or behavioral consequences of neonatal herpes simplex virus (HSV) infection, the method comprising:
   administering to a maternal subject an immunogenic product comprising one or more HSV antigens, wherein the maternal subject is HSV seronegative and the maternal subject is pregnant.

11. The method of claim 10, wherein the maternal subject is HSV seronegative.

12. The method of claim 10, wherein the immunogenic product is selected from the group consisting of an HSV protein or antigenic fragment thereof and a replication-impaired HSV.

13. The method of claim 12, wherein the replication-impaired HSV is dl5-29.

14. The method of claim 12, wherein the HSV protein is glycoprotein D (gD) of HSV.

15. A method for protecting offspring against neurological disease associated with neonatal herpes simplex virus (HSV) infection, the method comprising:
   administering to a pregnant subject an anti-HSV antibody, wherein the neurological disease associated with neonatal HSV infection is anxiety or a mood disorder and wherein the pregnant subject is HSV seronegative or has a latent HSV infection.

16. The method of claim 15, wherein the pregnant subject is HSV seronegative.

17. The method of claim 15, wherein the pregnant subject has a latent HSV infection.

18. The method of claim 15, wherein the anti-HSV antibody comprises:
   (i) a heavy chain variable region ($V_H$) having
      a $V_H$ CDR1 having an amino acid sequence of SEQ ID NO: 1,
      a $V_H$ CDR2 having an amino acid sequence of SEQ ID NO: 2, and
      a $V_H$ CDR3 having an amino acid sequence of SEQ ID NO: 3; and
   (ii) a light chain variable region ($V_L$) having
      a $V_L$ CDR1 having an amino acid sequence of SEQ ID NO: 4,
      a $V_L$ CDR2 having an amino acid sequence of SEQ ID NO: 5, and
      a $V_L$ CDR3 having an amino acid sequence of SEQ ID NO: 6.

19. The method of claim 15, wherein the anti-HSV antibody comprises a heavy chain variable region (VH) having an amino acid sequence of SEQ ID NO: 7 and a light chain variable region (VL) having an amino acid sequence of SEQ ID NO: 8.

20. The method of claim 15, wherein the anti-HSV antibody comprises:
   (i) a heavy chain variable region ($V_H$) having
      a $V_H$ CDR1 having an amino acid sequence of SEQ ID NO: 10,
      a $V_H$ CDR2 having an amino acid sequence of SEQ ID NO: 11, and
      a $V_H$ CDR3 having an amino acid sequence of SEQ ID NO: 12; and
   (ii) a light chain variable region ($V_L$) having
      a $V_L$ CDR1 having an amino acid sequence of SEQ ID NO: 13,
      a $V_L$ CDR2 having an amino acid sequence of SEQ ID NO: 14, and
      a $V_L$ CDR3 having an amino acid sequence of SEQ ID NO: 15.

21. The method of claim 15, wherein the anti-HSV antibody comprises a heavy chain variable region (VH) having an amino acid sequence of SEQ ID NO: 16 and a light chain variable region (VL) having an amino acid sequence of SEQ ID NO: 17.

22. The method of claim 15, wherein the anti-HSV antibody is administered to the maternal subject via vector-mediated delivery.

23. The method of claim 22, wherein the vector-mediated delivery is AAV vector-mediated delivery.

* * * * *

UNITED STATES PATENT AND TRADEMARK OFFICE
CERTIFICATE OF CORRECTION

| | |
|---|---|
| PATENT NO. | : 12,378,305 B2 |
| APPLICATION NO. | : 17/284427 |
| DATED | : August 5, 2025 |
| INVENTOR(S) | : Margaret E. Ackerman et al. |

It is certified that error appears in the above-identified patent and that said Letters Patent is hereby corrected as shown below:

In the Specification

Column 1, Line 16, after "FEDERALLY SPONSORED RESEARCH OR DEVELOPMENT" delete "Not applicable.," and insert -- This invention was made with government support under R01 EY009083 awarded by the National Institutes of Health. The government has certain rights in the invention. --.

This certificate supersedes the Certificate of Correction issued April 9, 2021.

Signed and Sealed this
Thirtieth Day of September, 2025

John A. Squires
*Director of the United States Patent and Trademark Office*

SEQUENCE LISTING

<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

Ser Asp Tyr Trp Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Asn Ile Lys Tyr Asp Gly Ser Glu Lys Tyr Tyr Val Asp Ser Val Lys
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Ala Gly Leu Leu Trp Phe Gly Glu Lys Ala Phe Asp Ile
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Ser Arg Tyr Leu Ala
1               5

<210> SEQ ID NO 5
<211> LENGTH: 11
<212> TYPE: PRT
<213> ORGANISM: Artificial Sequence
<220> FEATURE:
<223> OTHER INFORMATION: Sythetic polypeptide

<400> SEQUENCE: 5

Tyr Asp Ala Ser Asn Arg Ala Thr Gly Ile Pro
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Gln Gln Arg Arg Ser Trp Pro Pro Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Lys Tyr Asp Gly Ser Glu Lys Tyr Tyr Val Asp Ser Val
    50                  55                  60

Lys Gly Arg Phe Thr Thr Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Leu Leu Trp Phe Gly Glu Lys Ala Phe Asp Ile Trp Gly Gln
            100                 105                 110

Gly Thr Met Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Ser Trp Pro Pro
                85                  90                  95

Thr Phe Gly Gly Gly Thr Lys Val Glu Ile Lys
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

```
Ala Asp Pro Asn Arg
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Gly Gly Thr Leu Arg Thr Tyr Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 11

Thr Ile Pro Leu Phe Gly Lys Thr
1               5

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12

Ala Arg Asp Leu Thr Thr Leu Thr Ser Tyr Asn Trp Trp Asp Leu
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 13

Gln Ser Val Thr Ser Ser Gln
1               5

<210> SEQ ID NO 14
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 14

Gly Ala Ser
1

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Gln Gln Tyr Gly Ser Ser Pro Thr
1               5

<210> SEQ ID NO 16
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 16

```
Gln Val Thr Leu Lys Gln Ser Gly Ala Glu Val Lys Pro Gly Ser
1               5                   10                  15

Ser Val Lys Val Ser Cys Thr Ala Ser Gly Gly Thr Leu Arg Thr Tyr
            20                  25                  30

Gly Val Ser Trp Val Arg Gln Ala Pro Gly Gln Gly Leu Glu Trp Leu
        35                  40                  45

Gly Arg Thr Ile Pro Leu Phe Gly Lys Thr Asp Tyr Ala Gln Lys Phe
    50                  55                  60

Gln Gly Arg Val Thr Ile Thr Ala Asp Lys Ser Met Asp Thr Ser Phe
65                  70                  75                  80

Met Glu Leu Thr Ser Leu Thr Ser Glu Asp Thr Ala Val Tyr Tyr Cys
                85                  90                  95

Ala Arg Asp Leu Thr Thr Leu Thr Ser Tyr Asn Trp Trp Asp Leu Trp
            100                 105                 110

Gly Gln Gly Thr Leu Val Thr Val Ser
        115                 120
```

<210> SEQ ID NO 17
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 17

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Gln Leu Ala Trp Tyr Gln Gln Lys Pro Gly Gln Ala Pro Arg Leu Leu
        35                  40                  45

Ile Ser Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg
            100                 105
```

<210> SEQ ID NO 18
<211> LENGTH: 394
<212> TYPE: PRT
<213> ORGANISM: herpes simplex virus

<400> SEQUENCE: 18

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Val Asp Ala
            20                  25                  30

Ser Leu Lys Met Ala Asp Pro Asn Arg Phe Arg Gly Lys Asp Leu Pro
```

```
                35                  40                  45
Val Leu Asp Gln Leu Thr Asp Pro Pro Gly Val Arg Arg Val Tyr His
 50                  55                  60

Ile Gln Ala Gly Leu Pro Asp Pro Phe Gln Pro Ser Leu Pro Ile
 65                  70                  75                  80

Thr Val Tyr Tyr Ala Val Leu Glu Arg Ala Cys Arg Ser Val Leu Leu
                 85                  90                  95

Asn Ala Pro Ser Glu Ala Pro Gln Ile Val Arg Gly Ala Ser Glu Asp
                100                 105                 110

Val Arg Lys Gln Pro Tyr Asn Leu Thr Ile Ala Trp Phe Arg Met Gly
            115                 120                 125

Gly Asn Cys Ala Ile Pro Ile Thr Val Met Glu Tyr Thr Glu Cys Ser
            130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
                180                 185                 190

Val Lys Ile Asn Asp Trp Thr Glu Ile Thr Gln Phe Ile Leu Glu His
            195                 200                 205

Arg Ala Lys Gly Ser Cys Lys Tyr Ala Leu Pro Leu Arg Ile Pro Pro
210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
                260                 265                 270

Tyr Thr Ser Thr Leu Leu Pro Pro Glu Leu Ser Glu Thr Pro Asn Ala
            275                 280                 285

Thr Gln Pro Glu Leu Ala Pro Glu Asp Pro Glu Asp Ser Ala Leu Leu
            290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
                340                 345                 350

Ala Ala Leu Val Ile Cys Gly Ile Val Tyr Trp Met Arg Arg His Thr
            355                 360                 365

Gln Lys Ala Pro Lys Arg Ile Arg Leu Pro His Ile Arg Glu Asp Asp
            370                 375                 380

Gln Pro Ser Ser His Gln Pro Leu Phe Tyr
385                 390

<210> SEQ ID NO 19
<211> LENGTH: 393
<212> TYPE: PRT
<213> ORGANISM: herpes simplex virus

<400> SEQUENCE: 19

Met Gly Arg Leu Thr Ser Gly Val Gly Thr Ala Ala Leu Leu Val Val
 1               5                  10                  15
```

```
Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Arg Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390
```